US006673536B1

(12) United States Patent
Stoughton et al.

(10) Patent No.: US 6,673,536 B1
(45) Date of Patent: Jan. 6, 2004

(54) METHODS OF RANKING OLIGONUCLEOTIDES FOR SPECIFICITY USING WASH DISSOCIATION HISTORIES

(75) Inventors: Roland Stoughton, San Diego, CA (US); Julja Burchard, Kirkland, WA (US); Stephen H. Friend, Seattle, WA (US)

(73) Assignee: Rosetta Inpharmatics LLC., Kirkland, WA (US)

( * ) Notice: Subject to any disclaimer, the term of this patent is extended or adjusted under 35 U.S.C. 154(b) by 0 days.

(21) Appl. No.: 09/408,582

(22) Filed: Sep. 29, 1999

(51) Int. Cl.[7] .............................. C12Q 1/68; C12P 19/34; C07H 21/04
(52) U.S. Cl. ..................... 435/6; 435/91.1; 435/91.2; 536/23.1; 536/24.3
(58) Field of Search ........................... 435/6, 91.1, 91.2; 536/23.1, 24.3

(56) References Cited

U.S. PATENT DOCUMENTS

| | | | |
|---|---|---|---|
| 5,510,270 A | 4/1996 | Fodor et al. | |
| 5,556,752 A | 9/1996 | Lockhart et al. | |
| 5,569,588 A | 10/1996 | Ashby et al. | |
| 5,578,832 A | 11/1996 | Trulson et al. | |
| 5,716,785 A | 2/1998 | Van Gelder et al. | |
| 5,891,636 A | 4/1999 | Van Gelder et al. | |
| 6,171,794 B1 * | 1/2001 | Burchard et al. | ............... 435/6 |

FOREIGN PATENT DOCUMENTS

| WO | WO 98/41531 | 9/1998 |
|---|---|---|
| WO | WO 00/03039 | 1/2000 |

OTHER PUBLICATIONS

Stimpson et al., "Real–time detection of DNA hybridization and melting on oligonucleotide arrays by using optical guides," PNAS, 1995, vol. 92, pp. 6379–6383.*
Albretsen et al., 1988, "Optimal conditions for hybridization with oligonucleotides: a study with myc–oncogene DNA probes", Anal Biochem 170:193–202.
Anshelevich VV et al., 1984, "Slow relaxational processes in the melting of linear biopolymers: a theory and its application to nucleic acids", Biopolymers. Jan;23(1):39–58.
Ausubel et al., eds., 1989, Current Protocols in Molecular Biology, Vol I, Green Publishing Associates, Inc., John Wiley & Sons, Inc., New York, pp. 2.10.1–2.10.16.
Beattie et al., 1995, "Hybridization of DNA targets to glass–tethered oligonucleotide probes", Mo! Biotechnol 4:213–225.
Blanchard and Hood, 1996, "High–density oligonucleotide arrays", Biosensors and Bioelectronics 11:687–690.
Blanchard, 1998, "Synthetic DNA Arrays" in *Genetic Engineering, vol. 20* Setlow, J.K. (ed.) Plenum Press, New York, pp. 111–123.

Blanchard and Hood, 1996, "Sequence to array: probing the genome's secrets", Nat Biotechnol 14:1649.
Stimpson et al., 1995, "Real–time detection of DNA hybridization and melting on oligonucleotide arrays by using optical wave guides", Proc Natl Acad Sci USA 92:6379–6383.
Vernier et al., 1996, "Radioimager quantification of oligonucleotide hybridization with DNA immobilized on transfer membrane: application to the identification of related sequences", Anal Biochem 235:11–19.
Wang et al., 1995, "Origins of high sequence selectivity: a stopped–flow kinetics study of DNA/RNA hybridization by duplex– and triplex–forming oligonucleotides", Biochem 34:9774–9784.
Wetmur, 1991, "DNA probes: applications of the principles of nucleic acid hybridization", Crit Rev Biochem Mol Biol 26:227–259.
Young and Wanger, 1991, "Hybridization and dissociation rates of phosphodiester or modified oligodeoxynucleotides with RNA at near–physiological conditions", Nucleic Acids Res 19:2463–2470.
Day et al., 1995, "Electrophoresis for genotyping temporal: thermal gradient gel electrophoresis for profiling of oligonucleotide dissociation", Nucleic Acids Res 23:2404–2412.
DeRisi et al., 1996, "Use of a cDNA microarray to analyse gene expression patterns in human cancer", Nat Genet 14:457–460.
Fodor et al., 1991., "Light–directed, spatially addressable parallel chemical synthesis", Science 251:767–773.
Goffeau et al., 1996, "Life with 6000 genes", Science 274:546, 563–567.
Graves DJ., "Powerful tools for genetic analysis come of age", Trends Biotechnol. Mar 1999.;17(3):127–34.
Guo et al., 1997, "Enhanced discrimination of single nucleotide polymorphisms by artificial mismatch hybridization", Nat Biotechnol 15:331–335.
Hyndman et al., 1996, "Software to determine optimal oligonucleotide sequences based on hybridization simulation data", Biotechniques 20:1090–1097.

(List continued on next page.)

Primary Examiner—Jeffrey Siew
Assistant Examiner—Young Kim
(74) Attorney, Agent, or Firm—Pennie & Edmonds LLP

(57) ABSTRACT

The present invention provides methods and systems, particularly computer systems, for determining the relative specificity with which a particular polynucleotide molecule hybridizes to a polynucleotide probe. For example, the methods and systems of the invention enable a user to compare the specificity with which different polynucleotides hybridize to a given probe and/or rank these polynucleotides according to their specificity to that probe. The methods and systems of the invention also enable a user to compare the specificity with which a particular polynucleotide hybridizes to different probes, and/or rank those different probes according to their specificity for that particular polynucleotide.

110 Claims, 5 Drawing Sheets

OTHER PUBLICATIONS

Ikuta et al., 1987, "Dissociation kinetics of 19 base paired oligonucleotide–DNA duplexes containing different single mismatched base pairs", Nucleic Acids Res 15:797–811.

Kajimura et al., 1990, "Application of long synthetic oligonucleotides for gene analysis: effect of probe length and stringency conditions on hybridization specificity", Genet Anal Tech Appl 7:71–79.

Kunitsyn et al., 1996, "Partial thermodynamic parameters for prediction stability and washing behavior of DNA duplexes immobilized on gel matrix", J Biomol Struct Dyn 14:239–244.

Lockhart et al., 1996, "Expression monitoring by hybridization to high–density oligonucleotide arrays", Nat Biotechnol 14:1675–1680.

Maskos and Southern, 1992, "Oligonucleotide hybridizations on glass supports: a novel linker for oligonucleotide synthesis and hybridization properties of oligonucleotides synthesised in situ", Nucleic Acids Res 20:1679–1684.

Nicoloso et al., 1989, "Titration of variant DNA sequences differing by a single point–mutation by selective dot–blot hybridization with synthetic oligonucleotides", Biochem Biophys Res Comm 159:1233–1241.

Niemeyer et al., 1998, "Hybridization characteristics of biomolecular adaptors, covalent DNA—streptavidin conjugates", Bioconjug Chem 9:168–175.

Pease et al., 1994, "Light–generated oligonucleotide arrays for rapid DNA sequence analysis", Proc Natl Acad Sci USA 91:5022–5026.

Persson et al., 1997, "Analysis of oligonucleotide probe affinities using surface plasmon resonance: a means for mutational scanning", Anal Biochem 246:34–44.

Sambrook et al., eds., 1989, Molecular Cloning: A Laboratory Manual, 2nd Ed. Cold Spring Harbor Laboratory Press, Cold Spring Harbor, New York, pp. 9.47–9.51 and 11.55–11.61.

SantaLucia, 1988, "A unified view of polymer, dumbbell, and oligonucleotide DNA nearest–neighbor thermodynamics", Proc Natl Acad Sic USA 95:1460–1465.

Schena et al., 1995, "Quantitative monitoring of gene expression patterns with a complementary DNA microarray", Science 270:467–470.

Schena et al., 1996, "Parallel human genome analysis: microarray–based expression monitoring of 1000 genes", Proc Natl Acad Sci USA 93:10614–10619.

Shalon et al., 1996, "A DNA microarray system for analyzing complex DNA samples using two–color fluorescent probe hybridization", Genome Res 6:639–645.

* cited by examiner

METHODS OF RANKING OLIGONUCLEOTIDES FOR SPECIFICITY USING WASH DISSOCIATION HISTORIES

1. FIELD OF THE INVENTION

This invention relates to the field of nucleic acid hybridization. In particular, the present invention relates to methods for ranking the relative specificity with which polynucleotide probes hybridize to a nucleic acid sequence. The invention also relates to methods of identifying and/or designing nucleic acid sequences which hybridize most specifically to a nucleotide sequence of interest.

2. BACKGROUND

The ability to measure abundances of different nucleic acid molecular species in a sample containing many different nucleic acid sequences is a matter of great interest to many researchers. Presently, assays involving hybridization of nucleic acid molecules to a complementary probe are the only way to detect the presence of a particular sequence or sequences in a complex sample comprising many different nucleic acid sequences. For example, the nucleotide sequence similarity of a pair of nucleic acid molecules can be distinguished by allowing the nucleic acid molecules to hybride, and following the kinetic and equilibrium properties of duplex formation (see, e.g., Sambrook, J. et al., eds., 1989, *Molecular Cloning: A Laboratory Manual*, 2nd Ed., Cold Spring Harbor Laboratory Press, Cold Spring Harbor, N.Y., at pp. 9.47–9.51 and 11.55–11.61; Ausubel et al., eds., 1989, *Current Protocols in Molecular Biology*, Vol I, Green Publishing Associates, Inc., John Wiley & Sons, Inc., New York, at pp. 2.10.1–2.10.16; Wetmur, J. G., 1991, *Critical Reviews in Biochemistry and Molecular Biology* 26:227–259; Persson, B. et al., 1997, *Analytical Biochemistry* 246:34–44; Albretsen, C. et al., 1988, *Analytical Biochemistry* 170:193–202; Kajimura, Y. et al., 1990, *GATA* 7:71–79; Young, S. and Wagner, R. W., 1991, *Nucleic Acids Research* 19:2463–2470; Guo, Z. et al., 1997, *Nature Biotechnology* 15:331–335; Wang, S. et al., 1995, *Biochemistry* 34:9774–9784; Niemeyer, C. M. et al., 1998, *Bioconjugate Chemistry* 9:168–175).

Some of the most widely used techniques employ oligonucleotide "probes," (i.e., DNA molecules having a length up to about 100 bases and more typically fewer than about 50 bases) to selectively hybridize to, and thereby identify, nucleic acid sequences in a sample that contain complementary sequences. Many assays for detecting nucleic acid sequences in a sample comprise binding a set of nucleic acid probes to a solid support, permitting a labeled nucleic acid species to bind to the immobilized nucleic acid, washing off any unbound material, and detecting the bound, labeled sequence. For example, in blotting assays, such as dot or Southern Blotting, nucleic acid molecules may be first separated, e.g., according to size by gel electrophoresis, transferred and bound to a membrane filter such as a nitrocellulose or nylon membrane, and allowed to hybridize to a single labeled sequence (see, e.g., Nicoloso, M. et al., 1989, *Biochemical and Biophysical Research Communications* 159:1233–1241; Vernier, P. et al., 1996, *Analytical Biochemistry* 235:11–19). Other techniques have been developed to study the hybridization kinetics of polynucleotides immobilized in agarose or polyacrylamide gels (see, e.g., Ikuta S. et al., 1987, *Nucleic Acids Research* 15:797–811; Kunitsyn, A. et al., 1996, *Journal of Biomolecular Structure and Dynamics* 14:239–244; Day, I. N. M. et al., 1995, *Nucleic Acids Research* 23:2404–2412), as well as hybridization to polynucleotide probes immobilized on glass plates (Beattie, W. G. et al., 1995, *Molecular Biotechnology* 4:213–225) including oligonucleotide microarrays (Stimpson, D. I. et al., 1995, *Proc. Natl. Acad. Sci. U.S.A.* 92:6379–6383).

In DNA microarray expression assays, a complex mixture of labeled soluble sequences, derived, e.g., from genes in a population of cells, is analyzed by hybridization to another complex set of sequences which are separated into individual species, each bound separately to a solid support. The amount of labeled sequence bound to each sequence on the support is used as a measure of the level of expression of the species in the cells (see, e.g., Schena et al., 1995, *Science* 270:467–470; Lockhart et al., 1996, *Nature Biotechnology* 14:1675–1680; Blanchard et al., 1996, *Nature Biotechnology* 14:1649; Ashby et al., U.S. Pat. No. 5,569,588).

Equilibrium binding during hybridization of nucleic acids with complementary strands is related to (a) the similarity of the hybridizing sequences, (b) the concentration of the nucleic acid sequences, (c) the temperature, and (d) the salt concentration. Accordingly, it is well known that although hybridization is very selective for matching sequences, related sequences from other genes or gene fragments which are not perfectly complementary will still hybridize at some level. For oligonucleotide probes targeted at low-abundance species, or at species with closely related (i.e., homologous) molecular family members, such "cross-hybridization" can significantly contaminate and confuse the results of hybridization to the oligonucleotide probes. For example, cross-hybridization is a particularly significant concern in the detection of single nucleotide polymorphisms (SNP's) since the sequence to be detected (i.e., the particular SNP) must be distinguished from other sequences that differ by only a single nucleotide.

To some extent, cross-hybridization can be limited by regulating the temperature and salt conditions (i.e., the "stringency") of the hybridization or post-hybridization washing conditions. For example, "highly stringent" wash conditions may be employed so as to destabilize all but the most stable duplexes such that hybridization signals are obtained only from the sequences that hybridize most specifically, and are therefore the most homologous, to the probe. Exemplary highly stringent conditions comprise, e.g., hybridization to filter-bound DNA in 5×SSC, 1% sodium dodecyl sulfate (SDS), 1 mM EDTA at 65° C., and washing in 0.1×SSC/0.1% SDS at 68° C. (Ausubel et al., eds., 1989, *Current Protocols in Molecular Biology*, Vol. I, Green Publishing Associates, Inc., and John Wiley & Sons, Inc., New York, N.Y., at p. 2.10.3). Alternatively, "moderate-" or "low-stringency" wash conditions may be used to identify sequences which are related, not just identical, to the probe, such as members of a multi-gene family, or homologous genes in a different organism. Such conditions are well known in the art (see, e.g., Sambrook et al., supra; Ausubel, F. M. et al., supra). Exemplary moderately stringent wash conditions comprise, e.g., washing in 0.2×SSC/0.1% SDS at 42° C. (Ausubel et al., 1989, supra). Exemplary low-stringency washing conditions include, e.g., washing in 5×SSC or in 0.2×SSC/0.1% SDS at room temperature (Ausubel et al., 1989, supra).

However, the exact wash conditions that are optimal for any given assay will depend on the exact nucleic acid sequence or sequences of interest, and, in general, must be empirically determined. There is no single hybridization or washing condition which is optimal for all nucleic acid preparations and sequences. Indeed, even the most optimized conditions can only partially distinguish between competing sequences, especially when the competing sequences are quite similar, or when some of the competing sequences are present in excess amounts or at high concentrations.

Other existing techniques to minimize cross-hybridization involve the selection and use of particular oligonucleotide probes that are most specific for a particular target nucleic acid molecule of interest. For example, multiple different oligonucleotide probes which are complementary to different, distinct sequences of a target nucleic acid may be used (see, e.g., Lockhart et al. (1996) *Nature Biotechnology* 14:1675–1680; Graves et al. (1999) *Trends in Biotechnology* 17:127–134). In other techniques, the oligonucleotide probe is intentionally mismatched, and its hybridization to (or dissociation from) the target nucleic acid molecule is compared to that of the perfect match oligonucleotide probe so that a cross-hybridization component may be subtracted from the total hybridization signal (see, e.g., Graves et al., supra).

However, the use of techniques such as these generally requires some means for selecting those oligonucleotide sequences which hybridize most specifically to a particular target nucleic acid sequence of interest (i.e., with the least cross-hybridization). Existing numerical models of hybridization can, in principle, predict specificity given the sequence of an oligonucleotide probe as well as the sequences of all the components in the hybridizing sample and their relative abundances. However, such numerical models are still too crude to provide reliable results. Further, necessary inputs to such models such as sequence information, relative abundances, and hybridization conditions are frequently only approximately known if at all. There is an enormous need, therefore, for empirical methods, by which the most specific oligonucleotides may be chosen among the many possible candidates so that cross-hybridization may be limited.

Discussion or citation of a reference herein shall not be construed as an admission that such reference is prior art to the present invention.

3. SUMMARY OF THE INVENTION

The present invention relates to nucleic acid hybridization. In particular, the invention provides methods for determining the severity of cross-hybridization to a particular oligonucleotide probe. The methods of the invention can therefore be used to evaluate, in terms of an objective empirically calculated statistic, the specificity of a particular oligonucleotide probe relative to a "perfect match" reference hybridization. The methods of the invention can also be used to rank a plurality of oligonucleotide probes, by means of an objective, empirically calculated value or "metric," according to the relative specificity with which each probe hybridizes to a particular polynucleotide sequence in a sample. Thus, the methods of the present invention can be used to screen a plurality of oligonucleotide probes so that the most specific probe or probes for a particular polynucleotide sequence may be selected among the many possible candidates.

For any target polynucleotide sequence (e.g., a particular gene, mRNA, or cDNA sequence of interest) there are generally hundreds of thousands (i.e., ~$10^5$) of possible oligonucleotide probes, each of different length and/or sequence position, which could be used to detect the polynucleotide by hybridization. The present invention provides methods to efficiently select, according to an objective standard, the few, most specific oligonucleotides out of the enormous number of possible candidates. Thus, by using the methods of this invention, the skilled artisan can reduce the number of probes, e.g., on a microarray, for detecting a particular gene, thereby allowing more genes to be reported with a given number of probes. The methods and compositions of the invention relate, not only to the evaluation of individual polynucleotides, e.g., individual polynucleotide sequences, but also to the evaluation of sets of polynucleotides which have a particular specificity or a particular degree of complementarity to a particular probe. Such sets of polynucleotides are referred to herein as "polynucleotide sets."

The invention is based, at least in part, on the discovery that the difference in the integral (i.e., the area) between an actual dissociation curve and a reference dissociation curve is a monotonic function of the level of non-specific hybridization in the actual dissociation curve. Thus, for example, if a given reference dissociation curve represents hybridization to a particular probe with 100% specificity (i.e., hybridization with zero mismatches), then the area between this reference dissociation curve and an actual dissociation curve obtained for the particular probe indicates the level of non-specific or cross-hybridization to the particular probe (i.e., in the actual dissociation curve).

The present invention therefore provides methods and compositions which can be used to determine the level or extent of cross-hybridization to a probe. Specifically, and in more detail, the invention provides, in a first embodiment, a method for determining the specificity with which polynucleotide molecules hybridize to molecules of a given probe. The methods comprise comparing a dissociation curve representing dissociation of polynucleotide molecules from molecules of the given probe to a reference dissociation curve representing dissociation of the polynucleotide molecules from molecules of a reference probe. In one particular aspect of this first embodiment, the comparing of the dissociation curve to the reference dissociation curve comprises determining the value of a metric representing the difference between the dissociation curve and the reference dissociation curve, e.g., by subtracting the integral of the dissociation curve from the integral of the reference dissociation curve.

In a particular aspect of this first embodiment, the dissociation curve is provided by a method comprising: (a) contacting a polynucleotide sample to one or more molecules of the given probe under conditions which allow polynucleotide molecules in the polynucleotide sample to hybridize to the one or more molecules of the given probe; and (b) measuring the polynucleotide molecules hybridized to the one or more molecules of given probe over a time period wherein a detectable fraction of the polynucleotide molecules dissociates from the one or more molecules of the given probe. Methods of this particular aspect of the first embodiment are also provided wherein the step of measuring the polynucleotide molecules hybridized to the one or more molecules of the given probe comprises: (i) repeatedly washing the polynucleotide sample under conditions such that some fraction of the polynucleotide molecules dissociates from the one or more molecules of the given probe; and (ii) measuring the polynucleotide molecules that remain hybridized to the one or more molecules of the given probe after each washing.

In another particular aspect of the first embodiment of the invention, the reference dissociation curve is provided by a method comprising: (a) contacting a polynucleotide sample to one or more molecules of the reference probe sequence under conditions which allow polynucleotide molecules in the polynucleotide sample to hybridize to the one or more molecules of the reference probe sequence; and (b) measuring polynucleotide molecules hybridized to the one or more molecules of the reference probe over a time period wherein a detectable fraction of the particular polynucleotide molecules dissociates from the one or more molecules of the reference probe. Preferably, the reference probe is identical to the given probe in these methods. However, the invention also provides preferred aspects of the first embodiment wherein the reference probe is chosen to have a binding energy for a perfect match duplex which is similar to or identical to the binding energy of the given probe for a perfect match duplex.

The invention further provides aspects of the first embodiment wherein the polynucleotide molecules are differentially labeled, e.g., with a fluorescent dye such as fluorescein, rhodamine, texas red; with a fluorescent label such as FAM, JOE, ROX, HEX, TET, IRD40, IRD41, a cyamine dye (e.g., Cy2, Cy3, Cy3.5, Cy5, Cy5.5, Cy7 or FLUORX), a BODIPY dye (e.g., BODIPY-FL, BODIPY-TR, BODIPY-TMR, BODIPY-630/650, or BODIPY-650/670), or an ALEXA dye (e.g., ALEXA-488, ALEXA-532, ALEXA-546, ALEXA-568 or ALEXA-594); with a radioactive isotope such as $^{32}P$, $^{35}S$, $^{14}C$ or $^{125}I$; an electron rich molecule, such as ferritin, hemocyanin or colloidal gold; or with a first chemical group specifically complexed to the polynucleotide molecule, and wherein the first chemical group is detected by a method comprising contacting the first chemical group (e.g., avidin or streptavidin) with a second chemical group (e.g., biotin or iminobiotin) that (i) has binding affinity for the first chemical group, and (ii) is covalently linked to an indicator molecule.

Various aspects of the invention are provided wherein the polynucleotide molecules are naturally occurring polynucleotide molecules such as genomic DNA molecules isolated from cells or from an organism, or RNA molecules isolated from cells or from an organism. Aspects of the invention are also provided wherein the polynucleotide molecules are, e.g., RNA molecules expressed by a cell or organism (e.g., messenger RNA molecules), cDNA molecules derived therefrom or cRNA molecules derived therefrom. Aspects of the invention are further provided wherein the polynucleotide molecules are, e.g., synthetic nucleic acid molecules, such as cDNA or a cRNA molecules, or polynucleotide molecules synthesized by polymerase chain reaction. Aspects of the invention are also provided wherein the polynucleotide molecules comprise short polynucleotide molecules which are representative of a nucleic acid population of a cell.

In various aspects of the invention the probes are complementary, e.g., to a DNA sequence such as a genomic DNA sequence or a cDNA sequence, or to an RNA sequence such as a messenger RNA sequence or a cRNA sequence. Various aspects of the invention are also provided wherein the probe comprises a sequence of DNA analogues, a sequence of A analogues, STS's or SNP's.

Various aspects of the invention are further provided wherein the probe or probes are immobilized on a solid support or surface (e.g., a nylon membrane, a cellulose filter or a glass surface). In fact, a particularly preferred aspect of the invention is provided wherein the probe is part of an array of probes such as a microarray. In various aspects of the invention provided herein the microarray comprises polynucleotides that are binding sites for fewer than 50% of the genes in the genome of an organism or, alternatively, for at least 50%, at least 75%, at least 85%, at least 90%, or at least 99% of the genes in the genome of an organism. In various aspects of the invention provided herein the probe of the microarray comprises a polynucleotide sequence of between 200 and 50,000 bases in length or between 300 and 1,000 bases in length, or a single stranded polynucleotide sequence of between 4 and 200 bases in length, between and 150 bases in length, less than 40 bases in length (e.g. between 15 and bases in length), between 40 and 80 bases in length, between 40 and 70 bases in length, and between 50 and 60 bases in length. In various embodiments provided herein the microarray can comprise at least 500, at least 1,000, at least 1,500, at least 2,000, at least 2,500, at least 5,000, at least 10,000, at least 15,000, at least 20,000, at least 25,000, at least 50,000, or at least 55,000 different probes per 1 $cm^2$.

In still other embodiments described herein, the invention provides methods for comparing the specificity with which molecules of a first polynucleotide sequence hybridize to a probe to the specificity with which molecules of a second polynucleotide sequence hybridize to the probe. The method comprises determining the value of a metric by comparing a first dissociation curve representing dissociation of molecules of the first polynucleotide sequence from the probe to a second dissociation curve representing dissociation of molecules of the second polynucleotide sequence from the probe, wherein the metric is related to the specificity with which molecules of the first polynucleotide sequence hybridizes to the probe relative to molecules of the second polynucleotide sequence.

In yet other embodiments described herein, the invention provides methods for ranking two or more polynucleotide sequences by the specificity with which molecules of each of the two or more polynucleotide sequences hybridize to a probe. The method comprises ranking the two or more polynucleotide sequences according to values of a metric, wherein a value of the metric is determined from each of the two or more polynucleotide sequences by a method comprising comparing a dissociation curve representing dissociation of molecules of one of the two or more polynucleotide sequences from molecules of the probe to a reference dissociation curve representing dissociation of molecules of a reference polynucleotide sequence from molecules of the probe, and wherein the value of the metric for each of the two or more polynucleotide sequences is related to the specificity with which molecules of each of the two or more polynucleotide sequences hybridize to molecules of the probe.

In still other embodiments provided herein, the invention provides a method for comparing the specificity with which molecules of a polynucleotide sequence hybridize to molecules of a first probe to the specificity with which molecules of the polynucleotide sequence hybridize to molecules of a second probe. The method comprises determining the value of a metric by comparing a first dissociation curve representing dissociation of molecules of the polynucleotide sequence from molecules of the first probe to a second dissociation curve representing dissociation of molecules of the polynucleotide sequence from molecules of the second probe, wherein the metric is related to the specificity with which molecules of the polynucleotide sequences hybridize to the molecules of the first probe relative to the molecules of the second probe.

In other embodiments, the invention provides methods for ranking two or more probes by the specificity with which molecules of a polynucleotide sequence hybridize to molecules of each of the two or more probes. The methods comprise ranking the two or more probes according to values of a metric, wherein the value of the metric is determined for each of the two or more probes by a method comprising comparing a dissociation curve representing dissociation of molecules of the polynucleotide sequence from molecules of one of the two or more probes to a reference dissociation curve representing dissociation of molecules of the polynucleotide sequence from molecules of a reference probe, and wherein the value of the metric for each of the two or more probes is related to the specificity with which molecules of the polynucleotide sequence hybridize to molecules of each of the two or more probes.

In yet other embodiments, the invention provides computer systems that may be used to practice each of the above-described methods of the invention. Specifically, the invention provides various computer systems comprising a processor and a memory coupled to the processor and encoding one or more programs. The one or more programs encoded by the memory cause the processor to perform the methods of the invention. For example, in one embodiment the invention provides a computer system for determining the specificity with which polynucleotide molecules hybridize to molecules of a given probe. Specifically, in this first embodiment the programs cause the processor to perform a method comprising: (a) comparing a dissociation curve representing dissociation of polynucleotide molecules from molecules of the given probe to a reference dissociation curve representing dissociation of the polynucleotide molecules from a reference probe; and (b) determining the value of a metric from said comparing, wherein the metric represents the difference between the dissociation curve and the reference dissociation curve.

In another embodiment, the invention provides a computer system for comparing the specificity with which a first polynucleotide sequence hybridizes to a probe to the specificity with which a second polynucleotide sequence hybridizes to said probe. The computer system comprises a processor and a memory encoding one or more programs coupled to the process. The one or more programs cause the processor to perform a method comprising: (a) comparing a first dissociation curve representing dissociation of the first polynucleotide sequence from the probe to a second dissociation curve representing dissociation of the second polynucleotide sequence from the probe; and (b) determining the value of a metric from said comparison, wherein the metric represents the difference between the dissociation curve and the reference dissociation curve.

The invention also provides a computer system for comparing the specificity with which molecules of a first polynucleotide sequence hybridize to molecules of a probe to the specificity with which molecules of a second polynucleotide sequence hybridize to molecules of said probe. The computer system comprises a processor and a memory encoding one or more programs coupled to the processor. The one or more programs cause the processor to perform a method comprising: (a) comparing a first dissociation curve representing dissociation of molecules of the first polynucleotide sequence from molecules of the probe to a second dissociation curve representing dissociation of molecules of the second polynucleotide sequence from molecules of the probe; and (b) determining the value of a metric from said comparing, wherein the metric represents the difference between the first dissociation curve and the second dissociation curve.

The invention also provides a computer system for ranking two or more polynucleotide sequences according to the specificity with which molecules of each of the two or more polynucleotide sequences hybridize to molecules of a probe. The computer system comprises a processor, and a memory coupled to the processor and encoding one or more programs. The one or more programs cause the processor to perform a method comprising: (a) comparing each of two or more dissociation curves (each of the two or more dissociation curves representing dissociation of molecules of one of the two or more polynucleotide sequences from molecules of the probe) to a reference dissociation curve representing dissociation of molecules of a reference polynucleotide sequence from molecules of the probe; (b) determining the value of a metric for each of the two or more polynucleotide sequences from each of said comparings, the value of said metric for each of the two or more polynucleotide sequences representing the difference between each of the two or more dissociation curves and the reference dissociation curve; and (c) ranking the two or more polynucleotide sequences according to the value of the metric for each of the two or more polynucleotide sequences.

The invention also provides a computer system for comparing the specificity with which molecules of a polynucleotide sequence hybridizes to molecules of a first probe relative to the specificity with which molecules of said polynucleotide sequence hybridizes to molecules of a second probe. The computer system comprises a processor and a memory encoding one or more programs coupled to the processor. The one or more programs cause the processor to perform a method comprising: (a) comparing a first dissociation curve representing dissociation of molecules of the polynucleotide sequence from molecules of the first probe to a second dissociation curve representing dissociation of molecules of the polynucleotide sequence from molecules of the second probe; and (b) determining the value of a metric from said comparing, wherein the metric represents the difference between the first dissociation curve and the second dissociation curve.

The invention further provides a computer system for ranking two or more probes by the specificity with which molecules of a polynucleotide sequence hybridize to molecules of each of the two or more probes. The computer system comprises a processor and a memory encoding one or more programs coupled to the processor. The one or more programs cause the processor to perform a method comprising: (a) comparing each of two or more dissociation curves (each of the two or more dissociation curves representing dissociation of molecules of the polynucleotide sequence from molecules of one of the two or more probes) to a reference dissociation curve representing dissociation of molecules of the polynucleotide sequence from molecules of the probe; (b) determining the value of a metric for each of the two or more probes from each of said comparings, the value of said metric for each of the two or more probes representing the difference between each of the two or more dissociation curves and the reference dissociation curve; and (c) ranking the two or more probes according to the value of the metric for each of the two or more probes.

In still other embodiments, the invention provides computer program products for use in conjunction with a computer system (e.g., one of the above-described computer systems of the invention) having a processor and a memory connected to the processor. The computer program products of the invention comprise a computer readable storage medium having a computer program mechanism encoded or embedded thereon. The computer program mechanism can be loaded into the memory of the computer and cause the processor to execute the steps of the methods of the invention. For example, in one aspect of this embodiment, the computer program mechanism can cause the processor to execute the steps of: (a) comparing a dissociation curve representing dissociation of polynucleotide molecules from molecules of a given probe to a reference dissociation curve representing dissociation of the polynucleotide molecules from molecules of a reference probe; and (b) determining the value of a metric from said comparing, said metric representing the difference between the dissociation curve and the reference dissociation curve.

In another aspect, the computer program mechanism can cause the processor to execute the steps of: (a) comparing a first dissociation curve representing dissociation of molecules of a first polynucleotide sequence from molecules of a probe to a second dissociation curve representing dissociation of molecules of a second polynucleotide sequence from molecules of the probe; and (b) determining the value of a metric from said comparing, said metric representing the difference between the first dissociation curve and the second dissociation curve.

In yet another aspect, the computer program mechanism can cause the processor to execute the steps of: (a) comparing each of two or more dissociation curves (wherein each of the two or more dissociation curves represents dissociation of molecules of one of two or more polynucleotide sequences from molecules of a probe) to a reference dissociation curve representing dissociation of molecules of a reference polynucleotide sequence from molecules of the probe; (b) determining the value of a metric for each of the two or more polynucleotide sequences from each of said comparings, the value of said metrics for each of the two or more polynucleotide sequences representing the difference between each of the two or more dissociation curves and the reference dissociation curve; and (c) ranking the two or more polynucleotide sequences according to the value of the metric for each of the two or more polynucleotide sequences.

In still another aspect of this embodiment, the computer program mechanism can cause the processor to execute the steps of: (a) comparing a first dissociation curve representing dissociation of molecules of a polynucleotide sequence from molecules of a first probe to a second dissociation curve representing dissociation of molecules of the polynucleotide sequence from molecules of a second probe; and (b) determining the value of a metric from said comparing, said metric representing the difference between the first dissociation curve and the second dissociation curve.

In yet another aspect of this embodiment, the computer program mechanism can cause the processor to execute the steps of: (a) comparing each of two or more dissociation curves (wherein each of the two or more dissociation curves represents dissociation of molecules of a polynucleotide sequence from molecules of one of two or more probes) to a reference dissociation curve representing dissociation of molecules of the polynucleotide sequence from molecules of the probe; (b) determining the value of a metric for each of the two or more probes from each of said comparings, the value of said metric for each of the two or more probes representing the difference between each of the two or more dissociation curves and the reference dissociation curve; and (c) ranking the two or more probes according to the value of the metric for each of the two or more probes.

Each of these embodiments is described and enabled, in detail, in the sections hereinbelow, with reference to the following figures.

4. BRIEF DESCRIPTION OF THE DRAWINGS

FIG. 1 is a general illustration of exemplary methods of the present invention for ranking oligonucleotides for specificity.

FIG. 2 illustrates actual wash data obtained for the dissociation of a candidate oligonucleotide (Δ) and a perfect-match reference oligonucleotide (○) from a probe; the data are interpolated and normalized to provide a dissociation curve and a reference dissociation curve, respectively; the area between the normalized curves is an objective measure that can be used to rate the candidate oligonucleotide for specificity.

5. DETAILED DESCRIPTION

Figure 1:
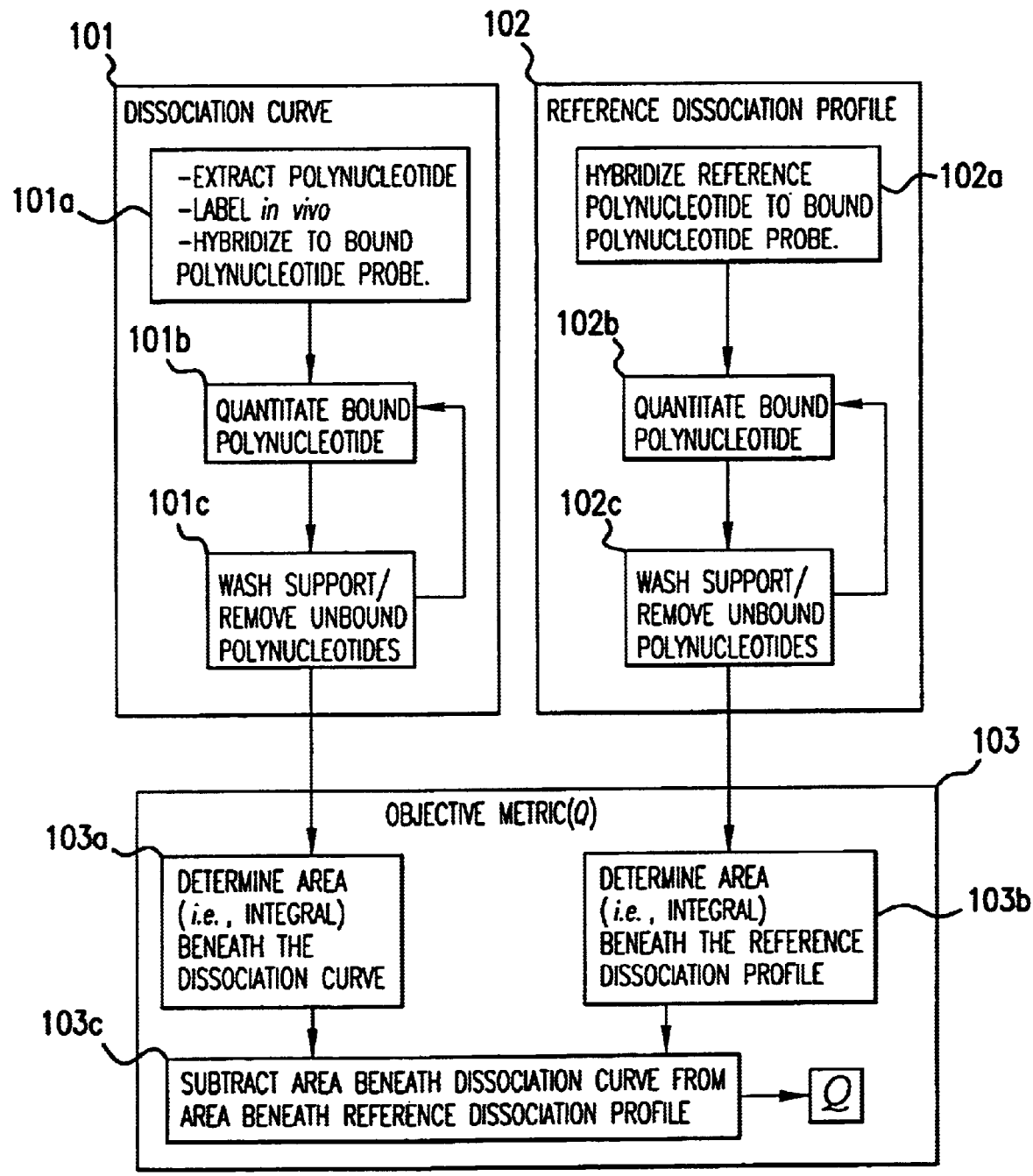

The present invention provides methods for determining the relative specificity with which polynucleotide sequences hybridize to a particular probe. That is to say, the methods of the present invention determine the specificity with which a polynucleotide sequence hybridizes to a particular probe compared to, e.g., the specificity with which the polynucleotide sequence hybridizes to one or more other probes or, alternatively, the specificity with which other polynucleotide sequences bind to the same probe. More specifically, the methods of the invention rank dissociation curves of a particular polynucleotide sequence or mixture of polynucleotide sequences from two or more probes by determining the value of an objective metric for each dissociation curve. The value of the objective metric for the dissociation curve of a polynucleotide sequence or mixture of polynucleotide sequences from a particular probe is directly related to the hybridization specificity of that particular probe for the polynucleotide sequence or sequences. Thus, the relative specificity of a particular probe is determined from the relative value of the objective metric evaluated for that probe; i.e., the relative specificity is determined by comparing the value of the objective metric evaluated for that probe to the values of the objective metric evaluated for the one or more other probes.

The polynucleotide molecules which may be analyzed by the methods of this invention include DNA molecules, such as, but by no means limited to genomic DNA molecules, cDNA molecules, and fragments thereof, such as oligonucleotides, expressed sequence tags (EST's), sequence tag sites (STS's), single nucleotide polymorphisms (SNP's), etc. Polynucleotide molecules which may be analyzed by the methods of this invention also include RNA molecules, such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof.

The extent to which any particular sequence initially hybridizes to a probe depends on several factors, including, for example, the level or degree of complementarity that sequence has to the sequence of the probe, the relative abundance of that sequence in the sample, the relative concentration and accessibility of the probe, and the extent to which hybridization has approached equilibrium. However, the kinetics of dissociation of the sequence from the probe depends only on the complementarity. In particular, a given polynucleotide sequence will dissociate from a particular probe according to a specific "dissociation curve" which can generally be characterized by a specific "dissociation-rate" or "off-rate." It is these dissociation curves which are used to rank the hybridization specificity.

The invention is largely described herein as being practiced using individual polynucleotide sequences. However, it is understood that the invention may also be practiced using sets of polynucleotide sequences which have a particular specificity or, more typically, a particular degree of complementarity to some particular probe (i.e., to some particular probe sequence). Such sets of polynucleotides are referred to herein as "polynucleotide sets." For example, a polynucleotide set of the invention can consist of polynucleotide molecules whose sequences have the same number of mismatches to a particular probe sequence. Thus, a first polynucleotide set of the invention can be, e.g., a set of polynucleotide molecules that have a single base-mismatch to a particular probe sequence. A second polynucleotide set of the invention can be, e.g., a set of polynucleotide molecules that have two base-mismatches to the particular probe sequence, and so forth. It is further understood that within such a polynucleotide set, the mismatches need not be in the same relative position of the polynucleotide sequence. Thus, a given polynucleotide set can, in fact, comprise a plurality of different polynucleotide sequences.

The present inventors have discovered that the difference in the integral (i.e., the area) between an actual dissociation curve and a reference dissociation curve is a monotonic function of the level of non-specific hybridization in the actual dissociation curve. Thus, for example, if a given reference dissociation curve represents hybridization to a particular probe with 100% specificity (i.e., hybridization with zero mismatches), then the area between this reference dissociation curve and an actual dissociation obtained for the particular probe indicates the level of non-specific hybridization or cross hybridization to the particular probe (i.e., in the actual dissociation curve).

The following subsections present the methods of the invention in greater detail. In particular, Section 5.1 first describes the general methods of the invention. Section 5.2 describes exemplary systems which may be used for implementing the analytical methods of the invention. Finally, Section 5.3 describes, in detail, exemplary systems and probes for measuring hybridization and/or cross hybridization levels of polynucleotide molecules.

These descriptions are by way of exemplary illustrations, in increasing detail and specificity, of the general methods of the invention. These examples are non-limiting, and related variants that will be apparent to one of skill in the art are intended to be encompassed by the appended claims. Following these examples are descriptions of embodiments of the data gathering steps that accompany the general methods.

5.1. Determining Hybridization Specificity

A flow chart illustrating an exemplary method of the present invention is shown in FIG. 1. This embodiment determines a dissociation curve (101) which is obtained or provided for polynucleotides hybridized to molecules of a particular (i.e., a "given") probe. One or more reference dissociation curves (102) are also obtained or provided for hybridization of polynucleotides to molecules of one or more "reference" probes.

Preferably, the reference probes are probes having a known specificity, or at least a known degree of complementarity, to a particular polynucleotide sequence (or to a particular polynucleotide set). In one preferred embodiment, the reference probes are probes that are completely complementary to a particular nucleic acid molecule (i.e., to polynucleotide molecules having a particular nucleic acid sequence) of interest to a user. However, the reference probes may also be, e.g., the same probe as the given probe, a probe identical to the given probe or a set of probes identical to the given probe. As the term is used herein, a set of probes is understood to consist of probes in which the dissociation of each polynucleotide sequence having a particular degree of complementary i to a probe is expected to be identical, or at least substantially identical, for each individual probe in the class of probes.

The dissociation curve for the polynucleotides is then compared to one or more reference dissociation curves to obtain an objective metric (103) related to the specificity of the probe. In one particular embodiment, the difference between the area (or integral) beneath the dissociation curve for the particular sample and the area (or integral) beneath the reference dissociation curve is evaluated. The objective metric related to the specificity of the probe then comprises this difference.

In particular embodiments of this invention, certain steps illustrated in FIG. 1 may be omitted or performed in orders other than as illustrated. For example, in certain embodiments the steps of obtaining a dissociation curve for a particular sample (101) and/or obtaining reference dissociation curves (102) will already be derived, e.g., for a certain probe or for a certain class of probes, and need not be performed separately for each analysis. In other embodiments, the step of obtaining reference dissociation curves (102) is performed concurrently with the step of obtaining a dissociation curve for a particular sample (101), e.g., by hybridizing differentially labeled polynucleotide samples to the probe or probes.

The following subsections describe, in detail, the methods of determining hybridization levels and obtaining dissociation curves (Section 5.1.1) and reference dissociation curves (Section 5.1.2) therefrom. The analysis methods of the invention are described in Section 5.1.3.

5.1.1. Determining Hybridization Levels

In order to practice the methods of the present invention, dissociation curves are obtained or provided for a sample or samples of polynucleotide molecules. Preferably, these samples comprise a mixture of different polynucleotide sequences, preferably having different specificities for a given probe, and preferably including one or more particular polynucleotide sequences of interest to a user. Preferably, the polynucleotide sequences for which dissociation curves are obtained hybridize to the given probe or probes at a level greater than about 1%, more preferably at a level greater than about 10%, still more preferably at a level greater than about 20%. In one, exemplary specific embodiment, the polynucleotides in the polynucleotide sample consist of a plurality of sets of polynucleotides. In another exemplary embodiment, all the polynucleotides in the polynucleotide sample that hybridize to the probe are part of a polynucleotide set in the sample.

The polynucleotide molecules may be from any source. For example, the polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as, for example, cDNA molecules, or polynucleotide molecules synthesized by PCR, RNA molecules synthesized by in vitro transcription, etc. The sample of polynucleotide molecules can comprise, e.g., molecules of DNA, RNA, or copolymers of DNA and RNA.

In preferred embodiments, the polynucleotide molecules to be analyzed are prepared in vitro from nucleic acids extracted from cells. For example, in one embodiment, RNA is extracted from cells (e.g., total cellular RNA), and messenger RNA is purified from the total extracted RNA. cDNA is then synthesized from the purified mRNA using, e.g. oligo-dT or random primers. In particularly preferred embodiments, the resulting cDNA molecules are transcribed to yield "cRNA" molecules (see, e.g., Van Gelder et al., 1998, U.S. Pat. No. 5,716,715; and Van Gelder et al., 1999, U.S. Pat. No. 5,891,636). Preferably, the polynucleotide molecules are short and/or fragmented polynucleotide molecules which are representative of the original nucleic acid population of the cell.

Preferably, the polynucleotide molecules to be analyzed by the methods of the invention are detectably labeled. The cDNA can be labeled directly, e.g., with nucleotide analogues, or a second, labeled cDNA strand can be made using the first strand as a template. Alternatively, the double-stranded cDNA can be transcribed into cRNA and labeled.

Preferably, the detectable label is a fluorescent label, e.g., by incorporation of nucleotide analogues. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}P$, $^{35}S$, $^{14}C$, and $^{125}I$. Fluorescent molecules suitable for the present invention include, but are not limited to, fluorescein and its derivatives, rhodamine and its derivatives, texas red, 5'-carboxy-fluorescein ("FAM"), 2',7'-dimethoxy-4',5'-dichloro-6-carboxy-fluorescein ("JOE"), N,N,N',N'-tetramethyl-6-carboxy-rhodamine ("TAMRA"), 6-carboxy-X-rhodamine ("ROX"), HEX, TET, IRD40, and IRD41. Fluorescent molecules which are suitable for the invention further include: cyamine dyes, including but not limited to Cy2, Cy3, Cy3.5, Cy5, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the polynucleotide may be labeled by specifically complexing a first group to the polynucleotide. A second group, covalently linked to an indicator molecule, and which has an affinity for the first group could be used to indirectly detect the polynucleotide. In such an embodiment, compounds suitable for use as a first group include, but are not limited to, biotin and iminobiotin. Compounds suitable for use as a second group include, but are not limited to, avidin and streptavidin.

The labeled polynucleotide molecules to be analyzed by the methods of the invention are contacted to a probe, or to a plurality of probes under conditions that allow polynucleotide molecules having sequences complementary to the probe or probes to hybridize thereto (FIG. 1, step 101a).

The probes of the invention comprise polynucleotide sequences which, in general, are at least partially complementary to at least some of the polynucleotide molecules to be analyzed. In particular, the probes are preferably complementary or partially complementary to one or more polynucleotide sequences of interest to a user. The polynucleotide sequences of the probe may be, e.g., DNA sequences, RNA sequences, or sequences of a copolymer of DNA and RNA. For example, the polynucleotide sequences of the probe may be full or partial sequences of genomic DNA, cDNA, or mRNA sequences extracted from cells. The polynucleotide sequences of the probes may also be synthesized oligonucleotide sequences. The probe sequences can be synthesized either enzymatically in vivo, enzymatically in vitro, e.g., by PCR, or non-enzymatically in vitro.

The probe or probes used in the methods of the invention are preferably immobilized to a solid support or surface such that polynucleotide sequences which are not hybridized or bound to the probe or probes may be washed off and removed without removing the probe or probes and any polynucleotide sequence bound or hybridized thereto. In one particular embodiment, the probes will comprise an array of distinct oligonucleotide sequences bound to a solid support or surface, such as a glass surface. Preferably, each particular oligonucleotide sequence is at a particular, known location on the surface. Alternatively, the probes may comprise double-stranded DNA comprising genes or gene fragments, or polynucleotide sequences derived therefrom, bound to a solid support or surface, such as a glass surface or a blotting membrane (e.g., a nylon or nitrocellulose membrane).

The conditions under which the polynucleotide molecules are contacted to the probe or probes preferably are selected for optimum stringency; i.e., under conditions of salt and temperature which create an environment close to the melting temperature for perfect match duplexes of the labeled polynucleotides and the probe or probes. For example, the temperature is preferably within 10–15° C. of the approximate melting temperature ("$T_m$") of a completely complementary duplex of two polynucleotide sequences (i.e., a duplex having no mismatches). Melting temperatures may be readily predicted for duplexes by methods and equations which are well known to those skilled in the art (see, e.g., Wetmur, 1991, *Critical Reviews in Biochemistry and Molecular Biology* 26:227–259), or, alternatively, such melting temperatures may be empirically determined using methods and techniques well known in the art, and described, e.g., in Sambrook, J. et al., eds., 1989, *Molecular Cloning: A Laboratory Manual*, 2nd Ed., Cold Spring Harbor Laboratory Press, Cold Spring Harbor, N.Y., at pp. 9.47–9.51 and 11.55–11.61; Ausubel et al., eds., 1989, *Current Protocols in Molecular Biology, Vol. I*, Green Publishing Associates, Inc., John Wiley & Sons, Inc., New York, at pp. 2.10.1–2.10.16. The exact conditions will depend on the specific polynucleotide molecules to be analyzed as well as on the particular probes, and may be determined by one of skill in the art (see, e.g., Sambrook et al., supra; Ausubel, F. M. et al., supra).

Hybridization times will most preferably be in excess of what is required for sampling of the bound polynucleotides (i.e., the probe or probes) by the labeled polynucleotides so that the mixture is close to equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein oligonucleotide arrays are used to probe a complex mixture of fragmented polynucleotides, typical hybridization times may be approximately 3–16 hours. Appropriate hybridization times for other embodiments will depend on the particular polynucleotide sequences and probes used, and may be determined by those skilled in the art (See, e.g., Sambrook, J. et al., supra).

After hybridization, generally the probe or probes are washed briefly, preferably in ice cold (i.e., approximately 0° C.) aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used (FIG. 1, 101b).

For example, in embodiments wherein fluorescently labeled nucleotides or nucleotide analogues are used, signal detection is conveniently accomplished simply by detecting a fluorescent signal at the wavelength emitted by the fluorophore, e.g., fluorescent imaging of labeled nucleotides hybridized or cross-hybridized to a probe array using a fluorescent scanner. In other embodiments, wherein the nucleotide or nucleotide analogues are labeled by means of radioactive isotopes, such as $^{32}P$ or $^{35}S$, hybridization may be detected by using autoradiography to detect the radioactive nucleotides. In yet other embodiments which use chemical labels such as biotin, the labeled polynucleotides may be detected, e.g., by means of a fluorescent probe or dye such as streptavidin.

The intensity of the measured signal from the label is an indicator of how many polynucleotide molecules have initially hybridized or bound to each probe, i.e., the hybridization "intensity" or hybridization "level". In general, the hybridization level of a particular probe includes both hybridization from perfect-match polynucleotide sequences, i.e., from polynucleotide sequences which hybridize to the probe with no mismatches, as well as cross-hybridization from partial-match or mismatch polynucleotide sequences, i.e., polynucleotide sequences having one or more mismatches to the probe.

After step 101b of measuring the initial hybridization level, the probe or probes are again washed (FIG. 1, step 101c), preferably in warm, low-salt solution (i.e., under conditions of low to moderate stringency) for some time interval (referred to herein as the "wash interval," $\tau$) so that the individual polynucleotide sequences fractionally dissociate from the probe at rates that are dependent upon their specificity or degree of complementarity to the probe. Exemplary wash conditions comprise 0.1 to 1 M salt concentration at a temperature of approximately 40° C. below the predicted melting temperature of a completely complementary duplex. The wash interval will generally be on the order of 1 second (e.g., $\tau \approx 1$ s), but may, alternatively, be as long as several minutes. The optimal wash interval will depend on the specific polynucleotide sequences, and/or the particular type of probe. Step 101b of imaging, described above, is then repeated, and the amount of detectable label is remeasured to determine the hybridization level after the wash interval, $\tau$.

Steps 101b and 101c of imaging and washing are repeated sequentially so that hybridization levels are measured over a plurality of wash intervals ($\tau_1, \tau_2, \ldots, \tau_N$), preferably until no detectable change is observed in the hybridization after subsequent washes. In a preferred embodiment, when no further change in the hybridization levels is observed after subsequent washes, the wash interval is approximately doubled (e.g., $\tau \approx 2$ s), and steps 101b and 101c are again sequentially repeated until there is no further loss of signal (i.e., no change in the hybridization levels is detected). In another preferred embodiment, the wash interval is then again increased, e.g., by a factor of approximately ten (e.g., $\tau \approx 10$ s), and steps 101b and 101c are again repeated until there is no further change detected in the hybridization levels. Preferably, at least four hybridization levels are measured over an equal number of wash intervals (i.e., $N \geq 4$). More preferably, hybridization levels are measured for ten or more wash intervals (i.e., $N \geq 10$). Still more preferably, hybridization levels are measured for 100 or more wash intervals (i.e., $N \geq 100$).

In preferred embodiments, there is no irreversible binding of the polynucleotides to the probe or surface, and the final hybridization level is zero. However, in certain less preferred embodiments, irreversible binding does occur, and the final hybridization level is not zero (i.e., some detectable level of labeled polynucleotides remains bound to the probe even after extensive washing). In such embodiments, the final hybridization level is subtracted from each measured hybridization level.

The resulting series of measured hybridization levels comprises a measure of the dissociation of the different hybridized and cross-hybridized polynucleotide sequences from the probe as a function of time, $t_n$, after each wash interval; i.e., $t_n = \tau_1 + \tau_2 + \ldots + \tau_n$. Thus, the resulting series of measured hybridization levels obtained by the above described method comprises the "dissociation curve" for the polynucleotide sample.

5.1.2. Obtaining Reference Dissociation Curves

According to the methods of the present invention, the dissociation curve of a given probe of interest is compared to a second dissociation curve. The second dissociation curve may be, e.g., a dissociation curve for the same polynucleotide sample dissociating from a second different probe or, alternatively, a dissociation curve for a different polynucleotide sample (e.g., a different polynucleotide sequence) dissociating from the same probe. Most generally, the second dissociation curve is a "reference dissociation curve," to which many different dissociation curves may be compared. The reference dissociation curve represents, e.g., dissociation of a particular polynucleotide sequence from the same probe as the dissociation curve or, alternatively, dissociation of the polynucleotide sample from a "reference" probe having a known specificity for a particular polynucleotide sequence or for a particular set of polynucleotide sequences.

The reference dissociation curves of the invention may be obtained or provided according to any of several different methods. Preferably, a reference dissociation curve is obtained or provided as outlined in FIG. 1 (step 102) by determining the dissociation curve, according to the methods described in Section 5.1.1 above, for polynucleotides hybridized to a reference probe. In one embodiment, the reference dissociation curve is obtained or provided in a separate hybridization assay with a reference probe, which may be different from the "given" probe, by determining the dissociation curve according to the methods of Section 5.1.1 above. More preferably, however, a given dissociation curve and a reference dissociation curve are obtained or provided simultaneously by measuring dissociation curves for a polynucleotide sample comprising two or more differentially labeled polynucleotide sequences, at least one of which is preferably a polynucleotide sequence of interest to a user.

For example, in one aspect of this embodiment, the polynucleotide sequences are each labeled with different fluorescent dyes which fluoresce at different wavelengths.

Thus, dissociation curves can be measured for each polynucleotide sequence, according to the methods of Section 5.1.1 above, by measuring fluorescence intensities for each wavelength.

In such an embodiment, the given probe and the reference probe are, in fact, the same probe. The given dissociation curve will be the dissociation curve of the entire polynucleotide sample (i.e., the dissociation of the two or more polynucleotide sequences), whereas the reference dissociation curve will be the dissociation curve of one of the differentially labeled polynucleotide sequences—e.g., a particular polynucleotide sequence of interest to a user. Because the dissociation of different polynucleotide sequences is measured simultaneously, this alternative embodiment is more stable to experimental error, and is therefore preferred.

In one preferred embodiment, the one or more reference dissociation curves are obtained or provided concurrently with the given dissociation curve for the polynucleotide sample of interest (i.e., the sample for which the cross-hybridization contribution(s) to the hybridization signal are to be determined). Specifically, the reference dissociation curve is obtained from the same probe (e.g., the same spot on a microarray) using a second, differentially labeled, simultaneous hybridization sample (e.g., using two-color fluorescence hybridization protocols) which contains a particular, specifically labeled polynucleotide sequence (e.g., a particular polynucleotide sequence of interest to a user, preferably the perfect-match species such as the target gene of interest or the complementary oligonucleotide sequence to an oligonucleotide probe).

In an alternative embodiment, the dissociation curves of the invention may be obtained or provided from the dissociation curves of individual polynucleotide sequences hybridizing or cross-hybridizing to a different, reference probe, such as a different oligonucleotide spot on an oligonucleotide array. In such an embodiment, the second probe is chosen to have a binding energy for the perfect match duplex which is similar or identical to the binding energy for the perfect match duplex of the first probe. Such binding energies may be readily predicted by those skilled in the art using numerical models which are well known in the art, including the nearest neighbor model (SantaLucia, J., 1988, *Proc. Natl. Acad. Sci. U.S.A.* 95:1460–1465), or by using computer implementations of such models, such as HybSimulator (Hyndman, D. et al., 1996, *Biotechniques* 20:1090–1097).

Still less preferably, the reference dissociation curves of the invention may also be obtained or provided by theoretical prediction of the form of the reference dissociation curves, with shape parameters adjusted to match known dissociation curves of an equivalent polynucleotide set (i.e., a set of polynucleotides having the same degree of complementarity to a probe), preferably obtained under the same hybridization conditions. An equivalent set of polynucleotides may include, e.g., polynucleotides which are complementary to and hybridize to similar but different probes, such as to a different oligonucleotide spot on an oligonucleotide array. In general, polynucleotides will hybridize with different binding energies, and their dissociation curves will therefore be characterized by different dissociation rates and dissociation times. Specifically, the dissociation time, $t_{diss}$, for a polynucleotide which hybridizes to a probe with a binding energy $\Delta G$ can be computed by Equation 1, below.

$$t_{diss} = \alpha \exp\left(\beta \frac{\Delta G}{RT}\right) \quad (1)$$

In Equation 1, above, R denotes the ideal gas constant. T is the temperature in Kelvin. The binding energy $\Delta G$ may be determined by any theoretical method or model which provides a value related to the actual binding energy. Such models include the nearest neighbor model (SantaLucia, J., 1988, supra), as well as computer implementations of such models, such as HybSimulator (Hyndman, D. et al., 1996, supra).

$\alpha$ and $\beta$ are fitting parameters which are fit to experimental data, e.g., from least squares fitting, for particular hybridization conditions. For example, it is expected that $\alpha$ and $\beta$ will have certain values for hybridization, e.g., to an oligonucleotide probe of a particular length in a microarray, and other, different values for hybridization under different conditions e.g., to an oligonucleotide probe in bulk solution.

In particular, $\alpha$ and $\beta$ may be determined by fitting Equation 1 (e.g., by linear regression; see, for example, Press et al., 1996, *Numerica Recipes in C*, 2nd Ed., Cambridge Univ. Press. Chapter 14, Section 2) to dissociation data from "equivalent" polynucleotide sets (e.g., other polynucleotides hybridizing to other, similar probes) with known or determined dissociation rates, $t_{diss}$, and binding energies $\Delta G$ which are known or may be calculated using well known theoretical models as discussed above.

Once appropriate values for $\alpha$ and $\beta$ have been determined, the dissociation time of a particular polynucleotide sequence hybridized to the particular probe of interest can be extrapolated from Equation 1 above using a value for the binding energy determined from a theoretical model as described above. A suitable dissociation curve can then be created, e.g., from a theoretical model, as discussed in Section 5.1.3 below, characterized by the determined dissociation time. In a particularly preferred embodiment, the dissociation curve is an exponential decay of the form $A(t)=\exp(-k_{diss} t)$, where the dissociation rate $k_{diss}=1/t_{diss}$.

5.1.3. Computational Methods

As explained above, dissociation curves for labeled polynucleotides hybridizing to molecules of a particular probe or probes are preferably provided by incrementally measuring hybridization intensity levels of polynucleotides hybridized to the probe molecules after each wash interval. In the following, the variable "M" refers generally to the measured signal from the detectably labeled polynucleotides which remain hybridized to a particular probe after washing (i.e., the hybridization level or intensity). In detail, $M_{i,n}^a$ represents the hybridization intensity of polynucleotide i on probe a after the n'th washing. Probe a may be, e.g., a particular probe such as a particular probe on a microarray, or, alternatively, a may indicate a particular class of probes.

In general, the hybridization level is specified as a function of time, $t_n$, measured from the time of initial hybridization. The time of the n'th wash interval is referred to as $\tau_n$. Thus, the time $t_n$ is the summation of wash intervals up to and including $\tau_n$.

$$t_n = \tau_1 + \tau_2 + \tau_3 + \ldots + \tau_n \quad (2)$$

Therefore, $M_i^a(t_n)$ is the hybridization intensity of polynucleotide i on probe a after time $t_n$ from the initial hybridization measurement, i.e., after the n'th wash. Preferably, $M^a(t_n)$ is normalized with respect to the initial hybridization intensity, so that $M^a(0)=1$.

The analytical methods of the present invention use one or more "reference" dissociation curves which are represented herein as D. As explained above, each polynucleotide i which hybridizes to a particular reference probe will dissociate from the probe with a particular reference dissociation curve, $D_i$, which reflects the amount of that polynucleotide that remains bound to the reference probe at some time, t, after hybridization. Reference dissociation curves are provided as described in Section 5.1.2 above, e.g., by measuring dissociation curves for a particular polynucleotide which hybridizes or cross-hybridizes to the probe. Thus, a reference dissociation curve $D_i^a(t_m')$ may be provided for the dissociation of a reference polynucleotide from probe a as a function of time $t_m'$ of the m'th wash after hybridization. As with the dissociation curves M, the reference dissociation curves are preferably normalized with respect to the initial hybridization level, i.e., so that $D(0)=1$.

In order to practice the analytical methods of the present invention, the dissociation curves and reference dissociation curves are preferably piece-wise continuous functions of the hybridization time t. Accordingly, in certain embodiments, it may be necessary to provide for interpolating the dissociation curves so that the dissociation curves are piece-wise continuous functions. Methods for interpolating functions such as the dissociation curves of the present invention are well known in the art, and are described, e.g., by Press et al. (1996, *Numerical Recipes in C*, 2nd Ed., see in particular Chapter 3: "Interpolation and Extrapolation").

In one embodiment, one or more of the dissociation curves are linearly interpolated. Thus, for any time t between the n'th and (n+1)'th was intervals (i.e., wherein $t_n < t < t_{n+1}$) the dissociation curve M of a particular probe is approximated by the linear function which runs through the points $M(t_n)$ and $M(t_{n-1})$. In particular, in such an embodiment M(t) may be provided by the equation $$M(t) = M(t_{n+1}) + \frac{M(t_n) - M(t_{n+1})}{t_{n+1} - t_n}(t_{n+1} - t) \quad (3)$$
$$= M(t_n) - \frac{M(t_n) - M(t_{n+1})}{t_{n+1} - t_n}(t - t_n)$$

Likewise, and as is readily appreciated by one skilled in the art, the reference dissociation curve(s) D may also be linearly interpolated, e.g., according to Equation 3 above.

Most preferably, one or more of the dissociation curves are interpolated by summing products of an appropriate spline interpolation function S multiplied by the measured data values, as illustrated for the dissociation curve M by the following equation.

$$M(t) = \sum_n S(t - t_n) M(t_n) \quad (4)$$

The variable "t" refers to an arbitrary value of the time after initial hybridization at which dissociation curve data are to be evaluated. In general, S may be any smooth, or at least piece-wise continuous, function of limited support having a width characteristic of the structure expected in the dissociation curve function. An exemplary width can be chosen to be the distance over which the response function being interpolated falls from 90% to 10% of its asymptotic value. Exemplary S functions include linear and Gaussian interpolation. It is readily appreciated by those skilled in the art that the above described spline interpolation function S may likewise be used to interpolate the reference dissociation curve(s) D of the invention.

Alternatively, in certain embodiments of the present invention, the dissociation curve data may be interpolated by approximating each curve by one or more parameterized functions, most preferably by a function corresponding to a particular theoretical model of hybridization. For example, as noted in Section 5.1.2 above, in a particularly preferred embodiment the dissociation curve $M_i^a$ of polynucleotide i from a particular probe a is or may be represented by an exponential decay function.

$$A_i^a(t) = e^{-k_i a t} \quad (2)$$

The dissociation rate $k_i^a$ is a property of the polynucleotide i as well as a property of the particular probe a. In one preferred embodiment, the dissociation rate is selected so that for each measured time $t_m'$ the sum of the squares of the differences between the measured normalized dissociation curve and the exponential decay function for each measured time interval is minimized.

$$\min_{\{k_i^a\}} \sum_m \left[ M_i^a(t_m') - \sum_i A_i^a(t_m') \right]^2 \quad (3)$$

This preferable parameter adjustment is well known in the art as a least squares fit of $M_i^a$ to $\Sigma A_i^a$ (see, e.g., Press et al., 1996, *Numerical Recipes in C*, 2nd Ed., Cambridge Univ. Press; in particular Chapters 10 and 14). Other, less preferable model function based methods may also be used, such as polynomial fitting by various known classes of polynomials. Such a method of interpolation may also be used to interpolate the reference dissociation curve D of a reference polynucleotide.

Figure 2:
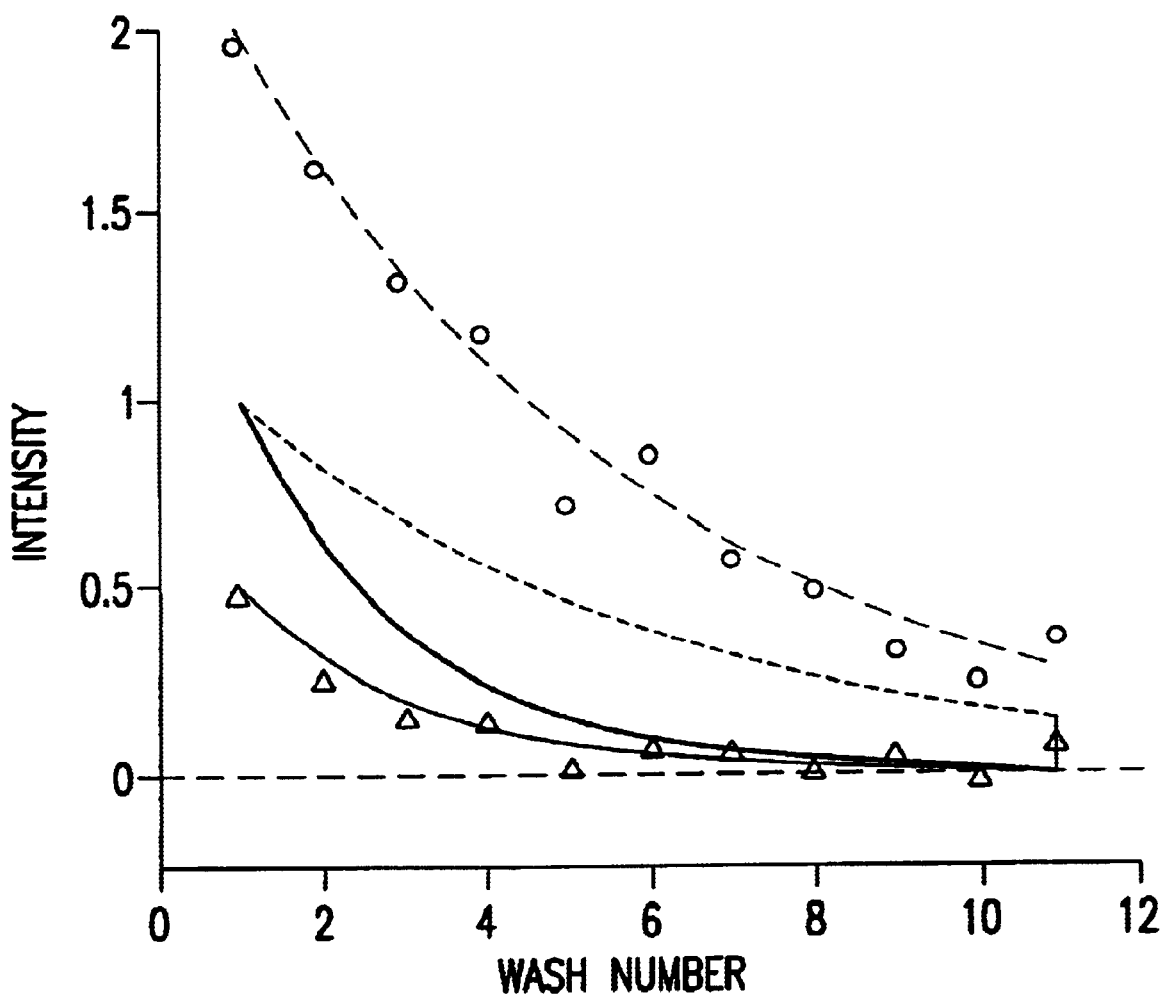

FIG. 2 illustrates exemplary dissociation curves, including an exemplary reference dissociation curve. Specifically, the triangles (Δ) indicate actual dissociation data from polynucleotide molecules hybridized to a given oligonucleotide probe. The open circles (○) represent dissociation data from the polynucleotides hybridized to a perfect-match, reference oligonucleotide probe. These data were interpolated by spline fitting according to Equation 4 above and normalized to obtain an actual or "given" dissociation curve and a reference dissociation curve, respectively.

Once piece-wise continuous reference dissociation curves and actual dissociation curves have been provided, the analytical methods of the invention then compare each of the dissociation curves to one or more of the reference dissociation curves so that an objective metric is thereby determined. The objective metric determined by this comparison is directly related to the specificity of the probe for which the dissociation curves have been obtained. In particular, the objective metric relates to the specificity of that probe to the polynucleotide for which the reference dissociation curve was obtained.

In a particularly preferred embodiment, the integral of the normalized dissociation curve is compared to the integral of the normalized reference dissociation curve. Specifically, the integral of the dissociation curve $M^a$ is subtracted from the integral of the reference dissociation curve $D_i$ to obtain the metric $Q_i^a$.

$$Q_i^a = \int_{t=0}^{t_N} D_i(t)\,dt - \int_{t=0}^{t_N} M_i^a(t)\,dt \quad (7)$$
$$= \int_{t=0}^{t_N} [D_i(t) - M_i^a(t)]\,dt$$

where $t_N$ is the final wash time for which the hybridization level has been determined in the dissociation curve $M^a$. Methods for evaluating integrals such as those in Equation 7 above are routine and well known to those skilled in the art. For example, the integrals of Equation 7 may be evaluated according to the numerical techniques described in Press et al. (1996, *Numerical Recipes in C*, 2nd Ed., Cambridge University Press, Chapter 4).

As one skilled in the art readily appreciates, the above method of comparing the integrals of an actual dissociation curve and a reference dissociation curve is identical to comparing the areas beneath those curves. In particular, the objective metric Q in Equation 7 above is equivalent to the difference in the areas beneath the reference dissociation curve and the actual dissociation curve. The metric Q obtained in Equation 7 is also equivalent to the area between the reference dissociation curve and the actual dissociation curve, wherein such an area is defined to be negative if the actual dissociation curve crosses above the reference dissociation curve. This area corresponds to the area between the two normalized splined curves in FIG. 2.

5.1.4. Uses of the Objective Metric

The objective metric $Q_i^a$ in Equation 7 above is a monotonic function of the fraction of non-specific hybridization intensity on probe a. Thus, smaller values of the objective metric indicate that probe a is relatively more specific to polynucleotide i, whereas higher values of the objective metric indicate that the probe is less specific for that polynucleotide.

The objective metric may be used, therefore, to evaluate and/or rank the relative specificity of a particular probe for different polynucleotides. In particular, given a set of different polynucleotides (i,j, m, n, etc.), one skilled in the art can readily evaluate, compare and/or rank the specificity of a particular probe a for each polynucleotide by comparing and/or ranking the value of the objective metric $Q^a$ for each polynucleotide. Thus, for example, if $Q_i^a < Q_j^a$, one skilled in the art would readily appreciate that probe a is more specific for polynucleotide i than for polynucleotide j. Likewise, the objective metric may also be used to evaluate and/or rank the relative specificity of different probes for the same polynucleotide. For example, given a set of probes (a, b, c, etc.), one skilled in the art can readily evaluate, compare and/or rank the specificity of each probe for a particular polynucleotide i by comparing and/or ranking the value of the objective metric $Q_i$ for each probe. Thus, for example, if $Q_i^a < Q_i^b$, one skilled in the art would readily appreciate the probe a is more specific for polynucleotide i than is probe b.

Because those probes which are most specific for a particular polynucleotide are generally best suited for detection of the particular polynucleotide by hybridization, the objective metric of the present invention may also be used to select a probe or probes out of two or more candidate probes for detecting a particular polynucleotide i by hybridization. Specifically, the probe or probes for detecting the particular polynucleotide are selected by selecting those probes having the lowest value of the objective metric $Q_i$ for the particular polynucleotide.

Given the teachings herein, variations of the objective metric Q from Equation 7 above are readily apparent to those skilled in the art. Such variations are also encompassed by the present invention. For example, one skilled in the art will readily appreciate that two dissociation curves may also be compared by means of the objective metric.

$$Q = \int_{t=0}^{t_N} [M_i^a(t) - M_j^b(t)] dt \qquad (8)$$

For example, the metric Q provided by Equation 8 may be used in embodiments wherein different probes are being compared by their specificity for the same polynucleotide (i.e., wherein i=j, and a≠b). The metric Q provided in Equation 8 may also be used in embodiments wherein different polynucleotides are being compared by their specificity for the same probe (i.e. wherein i≠j, and a=b).

One skilled in the art will also appreciate that the inverse of the objective metric from Equation 7, i.e., $1/Q_i^a$ may also be used as an objective metric to compare and/or rank hybridization specificities. As one skilled in the art readily appreciates, relatively large values of $1/Q_i^a$ indicate that a particular probe a is relatively specific for a particular polynucleotide i, whereas smaller values of $1/Q_i^a$ indicate that the probe is less specific for the polynucleotide. Thus, the objective metric $1/Q_i^a$ may likewise be used, e.g., to evaluate and/or rank the relative specificity of a particular probe for different polynucleotides, to evaluate and/or rank the relative specificity of different probes for the same polynucleotide, and to select a probe or probes for detecting a particular polynucleotide.

5.2. Implementation Systems and Methods

Figure 3:
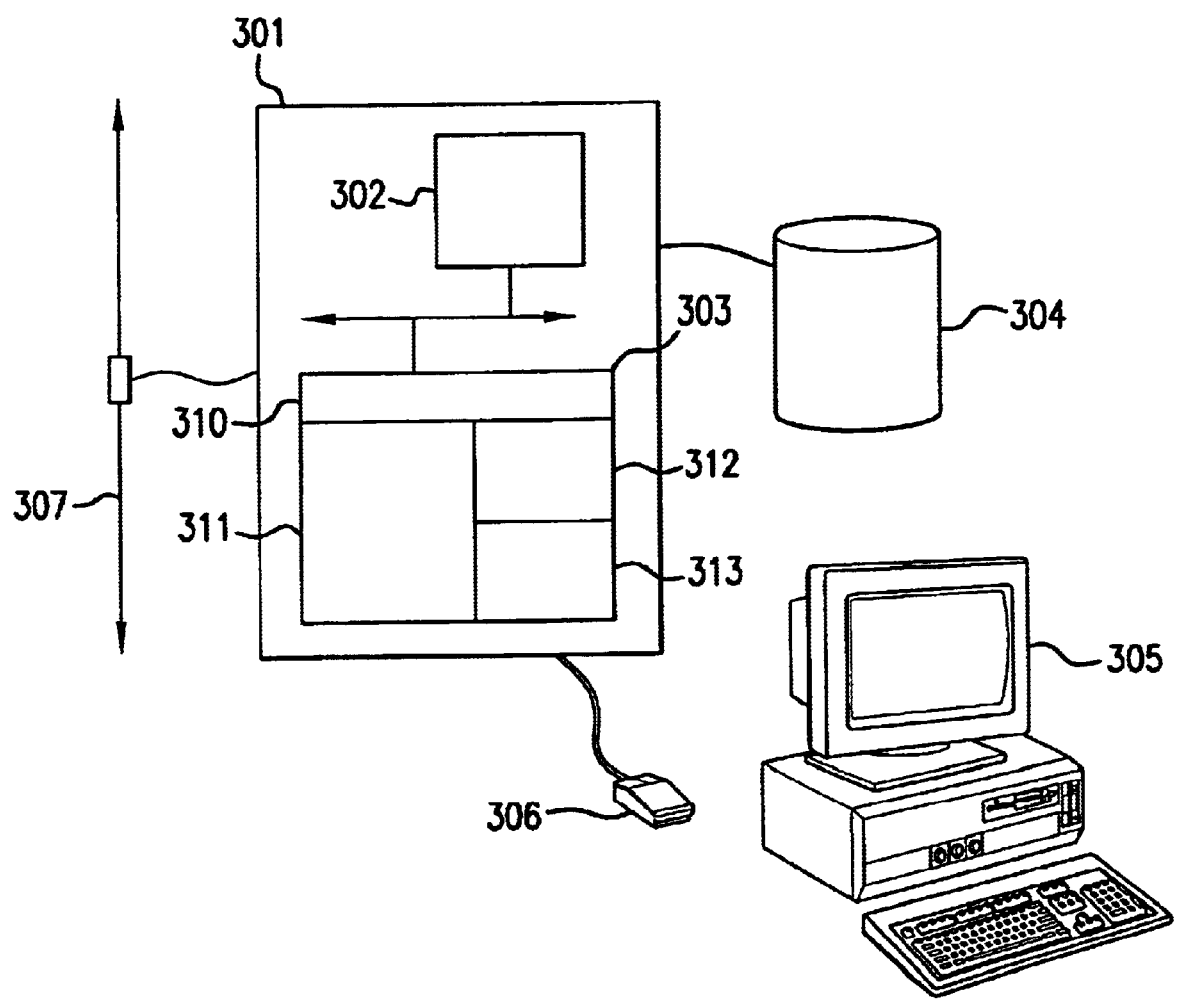
FIG. 3 illustrates an exemplary computer system for implementing the analytic methods of the invention.

The analytic methods described in the previous subsections can preferably be implemented by use of the following computer systems, and according to the following methods. FIG. 3 illustrates an exemplary computer system suitable for implementation of the analytic methods of this invention. Computer system 301 is illustrated as comprising internal components and being linked to external components. The internal components of this computer system include processor element 302 interconnected with main memory 303. For example, computer system 301 can be an Intel Pentium-based processor of 200 MHz or greater clock rate and with 32 MB or more of main memory.

The external components include mass storage 304. This mass storage can be one or more hard disks which are typically packaged together with the processor and memory. Such hard disks are typically of 1 GB or greater storage capacity. Other external components include user interface device 305, which can be a monitor and a keyboard, together with pointing device 306, which can be a "mouse", or other graphical input devices (not illustrated). Typically, computer system 301 is also linked to a network link 307, which can be part of an Ethernet link to other local computer systems, remote computer systems, or wide area communication networks, such as the Internet. This network link allows computer system 301 to share data and processing tasks with other computer systems.

Loaded into memory during operation of this system are several software components, which are both standard in the art and special to the instant invention. These software components collectively cause the computer system to function according to the methods of the invention. The software components are typically stored on mass storage 304. Software component 310 represents an operating system, which is responsible for managing computer system 301 and its network interconnections. This operating system can be, for example, of the Microsoft Windows™ family, such as Windows 95, Windows 98, or Windows NT, or, alternatively, a Macintosh operating system, or a Unix operating system. Software component 311 represents common languages and functions conveniently present in the system to assist programs implementing the methods specific to this invention. Languages that can be used to program the analytic methods of the invention include, for example, C, C++, and, less preferably, FORTRAN, PASCAL, BASIC, and JAVA. Most preferably, the methods of this invention are programmed in mathematical software packages which allow symbolic entry of equations and high-level specification of processing, including algorithms to be used, thereby freeing a user of the need to procedurally program individual equations and algorithms. Such packages include, e.g., Matlab from Mathworks (Natick, Mass.), Mathematica from Wolfram Research (Champaign, Ill.), or S-Plus from Math Soft (Seattle, Wash.). Accordingly, software component 312 represents the analytic methods of this invention as programmed in a procedural language or symbolic package.

In a preferred embodiment, the computer also contains a software component 313 which may be additional software for determining (i.e., calculating) a reference dissociation curve for a specific polynucleotide hybridizing to a particular probe. Such a reference dissociation curve will then be calculated according to the methods described in Section 5.1.2 above. Alternatively, software component 313 may also be a database of reference dissociation curves of polynucleotides. Such a database may comprise, for example, the dissociation rates and/or dissociation times corresponding to a plurality of polynucleotides hybridizing to a particular probe, a particular class of probes or, more preferably, a plurality of probes and/or a plurality of classes of probes.

In an exemplary implementation, to practice the methods of the present invention, hybridization level data (i.e., one or more actual dissociation curves) is first loaded in the computer system 301. These data can be directly entered by the user from monitor and keyboard 305, or from other computer systems linked by network connection 307, or on removable storage media such as a CD-ROM or floppy disk (not illustrated). Next the user causes execution of analysis software 312 which performs the steps of determining an objective metric, according to the methods described above, for the specificity of hybridization in each actual dissociation curve relative to a reference dissociation curve. Reference dissociation curves may be directly entered by the user, or, alternatively, may be calculated by or extracted from the database of software component 313.

The analytical software component 312 may also perform steps of comparing hybridization data (i.e., actual dissociation curves) for different probes and/or for different polynucleotides as described above in Section 5.1.4. For example, the analytical software component may perform steps of ranking and/or comparing the specificity of one or more probes for a particular polynucleotide. The analytical software component may also perform steps of ranking and/or comparing the specificity of a particular probe for different polynucleotides. The analytical software component may also perform steps of selecting a probe or probes for detecting a particular polynucleotide by hybridization.

The analytical systems of the invention also include computer program products that contain one or more of the above-described software components such that the software components may be loaded into the memory of a computer system. Specifically, a computer program product of the invention includes a computer readable storage medium having one or more computer program mechanisms embedded or encoded thereon in a computer readable format. The computer program mechanisms encoded, e.g., one or more of the analytical software components described above which can be loaded into the memory of a computer system 301 and cause the processor of the computer system to execute the analytical methods of the present invention.

The computer program mechanisms or mechanisms are preferably stored or encoded on a computer readable storage medium. Exemplary computer readable storage media are discussed above and include, but are not limited to: a hard drive, which may be, e.g., an external or an internal hard drive of a computer system of the invention, or a removable hard drive; a floppy disk; a CD-ROM; or a tape such as a DAT tape. Other computer readable storage media will also be apparent to those skilled in the art that can be used in the computer program mechanisms of the present invention.

The present invention also provides databases of reference dissociation curves for use in determining the objective metric of the invention. The databases of this invention include reference dissociation curves for a plurality of polynucleotides corresponding to a plurality of levels of complementarity to a particular probe, or, more generally, to a particular class of probes (e.g., for oligonucleotide microarrays). More preferably, the database includes dissociation curves for several probes, or, still more preferably, for several classes of probes. Preferably, such a database will be in an electronic form that can be loaded into a computer system 301. Such electronic forms include databases loaded into the main memory 303 of a computer system used to implement the methods of this invention, or in the main memory of other computers linked by network connection 307, or embedded or encoded on mass storage media 304, or on removable storage media such as a CD-ROM or floppy disk (not illustrated).

Alternative systems and methods for implementing the analytic methods of this invention are intended to be comprehended within the accompanying claims. In particular, the accompanying claims are intended to include the alternative program structures for implementing the methods of this invention that will be readily apparent to one of skill in the art.

5.3. Measurement of Hybridization Levels

In general, the hybridization methods of the present invention can be performed using any probe or probes which comprise a polynucleotide sequence and which are immobilized to a solid support or surface. For example, as described above, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probe may be full or partial sequences of genomic DNA or mRNA derived from cells, or may be cDNA or cRNA sequences derived therefrom. The polynucleotide sequences of the probes may also be synthetic nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support or surface which may be either porous or non-porous. For example, the probes of the invention may be polynucleotide sequences which are attached to a nitrocellulose or nylon membrane or filter. Such hybridization probes are well known in the art (see, e.g., Sambrook et al., Eds., 1989, *Molecular Cloning: A Laboratory Manual*, Vols. 1–3, 2nd ed., Cold Spring Harbor Laboratory, Cold Spring Harbor, N.Y.). Alternatively, the solid support or surface may be a glass or plastic surface.

5.3.1. Microarrays Generally

In a particularly preferred embodiment, hybridization levels are measured on microarrays of probes consisting of a solid phase on the surface of which are immobilized a population of polynucleotides, such as a population of DNA or DNA mimics or, alternatively, a population of RNA or RNA mimics. The solid phase may be a nonporous or, optionally, a porous material such as a gel. Microarrays can be employed, e.g., for analyzing the transcriptional state of a cell such as the transcriptional states of cells exposed to graded levels of a drug of interest or to graded perturbations to a biological pathway of interest. Microarrays are particularly useful in the methods of the instant invention in that they can be used to simultaneously screen a plurality of different probes to evaluate, e.g., each probe's sensitivity and specificity for a particular target polynucleotide.

In preferred embodiments, a microarray comprises a support or surface with an ordered array of binding (e.g., hybridizing) sites, e.g., for a plurality of different probes. Microarrays can be made in a number of ways, of which several are described hereinbelow. However produced, microarrays share certain characteristics: The arrays are reproducible, allowing multiple copies of a given array to be produced and easily compared with each other. Preferably, the microarrays are made from materials that are stable under binding (e.g., nucleic acid hybridization) conditions. The microarrays are preferably small, e.g., between about 5 cm$^2$ and 25 cm$^2$, preferably about 12 to 13 cm$^2$. However, both larger and smaller arrays are also contemplated and may be preferable, e.g., for simultaneously evaluating a very large number of different probes.

Preferably, a given binding site or unique set of binding sites in the microarray will specifically bind (e.g., hybridize) to the product of a single gene or gene transcript from a cell or organism (e.g., to a specific mRNA or to a specific cDNA derived therefrom). However, as discussed above, in general other, related or similar sequences will cross hybridize to a given binding site.

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface).

Preferably, the density of probes on a microarray is about 100 different (i.e., non-identical) probes per 1 cm$^2$ or higher. More preferably, a microarray used in the methods of the invention will have at least 550 probes per 1 cm$^2$, at least 1,000 probes per 1 cm$^2$, at least 1,500 probes per 1 cm$^2$ or at least 2,000 probes per 1 cm$^2$. In a particularly preferred embodiment, the microarray is a high density array, preferably having a density of at least about 2,500 different probes per 1 cm$^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (i.e., a matrix) in which each position represents a discrete binding site for a product encoded by a gene (i.e., for an mRNA or for a cDNA derived therefrom). For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer, a full length cDNA, a less-than full length cDNA, or a gene fragment.

Preferably, the microarrays used in the invention have binding sites (i.e., probes) for one or more genes relevant to the action of a drug of interest or in a biological pathway of interest. A "gene" is identified as an open reading frame (ORF) that encodes a sequence of preferably at least 50, 75, or 99 amino acid residues from which a messenger RNA is transcribed in the organism or in some cell or cells of a multicellular organism. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, *Science* 274:546–567). In contrast, the human genome is estimated to contain approximately 10$^5$ genes.

5.3.2. Preparing Probes for Microarrays

As noted above, the "probe" to which a particular target polynucleotide molecule specifically hybridizes according to the invention is a complementary polynucleotide sequence to the target polynucleotide. In one embodiment, the probes of the microarray comprise sequences greater than 500 nucleotide bases in length that correspond to a gene or gene fragment. For example, such probes can comprise DNA or DNA "mimics" (e.g., derivatives and analogs) corresponding to at least a portion of one or more genes in an organism's genome. In another embodiment, such probes are complementary RNA or RNA mimics.

DNA mimics are polymers composed of subunits capable of specific, Watson-Crick-like hybridization with DNA, or of specific hybridization with RNA. For example, the DNA mimics can comprise nucleic acids modified at the base moiety, at the sugar moiety, or at the phosphate backbone. For example, one particular DNA mimic includes, but is not limited to, phosphorothioates.

Such DNA sequences can be obtained, e.g., by polymerase chain reaction (PCR) amplification of gene segments from, e.g., genomic DNA, mRNA (e.g., from RT-PCR) or from cloned sequences. PCR primers are preferably chosen based on known sequences of the genes or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically, each probe on the microarray will be between about 20 bases and about 50,000 bases, and usually between about 300 bases and about 1,000 bases in length. PCR methods are well known in the art and are described, e.g., by Innis et at., eds., 1990, *PCR Protocols: A Guide to Methods and Applications*, Academic Press, Inc., San Diego, Calif. As will be apparent to one skilled in the art, controlled robotic systems are useful for isolating and amplifying nucleic acids.

An alternative, preferred means for generating the polynucleotide probes for a microarray used in the methods and compositions of the invention is by synthesis of synthetic polynucleotides or oligonucleotides, e.g, using N-phosphonate or phosphoramidite chemistries (Froehler et al., 1986, *Nucleic Acid Res.* 14:5399–5407; McBride et al., 1983, *Tetrahedron Lett.* 24:246–248). Synthetic sequences are typically between about 4 and about 500 bases in length, more typically between about 4 and about 200 bases in length, and even more preferably between about 15 and about 150 bases in length. In embodiments wherein shorter oligonucleotide probes are used, synthetic nucleic acid sequences less than about 40 bases in length are preferred, more preferably between about 15 and about 30 bases in length. In embodiments wherein longer oligonucleotide probes are used, synthetic nucleic acid sequences are preferably between about 40 and 80 bases in length, more preferably between about 40 and 70 bases in length and even more preferably between about 50 and 60 bases in length. In some embodiments, synthetic nucleic acids include non-natural bases, such as, but not limited to, inosine. As noted above, nucleic acid analogs may be used as binding sites for hybridization. An example of a suitable nucleic acid analog is peptide nucleic acid (see, e.g., Egholm et al., 1993, *Nature* 363:566–568; U.S. Pat. No. 5,539,083).

In other alternative embodiments, the hybridization sites (i.e., the probes) are made from plasmid or phage clones of genes, cDNAs (e.g., expressed sequence tags), or inserts therefrom (see, e.g., Nguyen et al., 1995, *Genomics* 29:207–209).

5.3.3. Attaching Probes to the Solid Surface

The probes are preferably attached to a solid support or surface which may be made, e.g., from glass, plastic (e.g., polypropylene, nylon) polyacrylamide, nitrocellulose, a gel, or other porous or nonporous material. A preferred method for attaching the nucleic acids to the surface is by printing on glass plates, as is described generally by Schena et al., 1995, *Science* 270:467–470. This method is especially useful for preparing microarrays of cDNA (see also DeRisi et al., 1996, *Nature Genetics* 14:457–460; Shalon et al., 1996, *Genome Res.* 6:639–645; and Schena et al., 1995, *Proc. Natl. Acad. Sci. U.S.A.* 93:10539–11286).

Another preferred method for making microarrays is by making high-density oligonucleotide arrays. Techniques are known for producing arrays containing thousands of oligonucleotides complementary to defined sequences and at defined locations on a surface using photolithographic techniques for synthesis in situ (see Fodor et al., 1991, *Science* 251:767–773; Pease et al., 1994, *Proc. Natl. Acad. Sci. U.S.A.* 91:5022–5026; Lockhart et al., 1996, *Nature Biotechnology* 14:1675; U.S. Patent Nos. 5,578,832; 5,556,752; and 5,510,270) or other methods for rapid synthesis and deposition of defined oligonucleotides (Blanchard et al., *Biosensors & Bioelectronics* 11:687–690). When these methods are used oligonucleotides (e.g., 25-mers) of known sequence are synthesized directly on a surface such as a derivatized glass slide. Usually, the array produced is redundant with several oligonucleotide molecules per RNA. Oligonucleotide probes can also be chosen to detect particular alternatively spliced mRNAs.

Other methods for making microarrays, e.g., by masking (Maskos and Southern, 1992, *Nucl. Acids. Res.* 20:1679–1684) can also be used. In principle and as noted above any type of array, for example dot blots on a nylon hybridization membrane (see Sambrook et al., supra) can be used. However, as will be recognized by those skilled in the art, very small arrays will frequently be preferred because hybridization volumes will be smaller.

In a particularly preferred embodiment, microarrays used in the invention are manufactured by means of an ink jet printing device for oligonucleotide synthesis, e.g., using the methods and systems described by Blanchard in International Patent Publication No. WO 98/41531, published on Sep. 24, 1998; Blanchard et al., 1996, *Biosensors and Bioeletronics* 11:687–690; Blanchard, 1998, in *Synthetic DNA Arrays in Genetic Engineering*, Vol. 20, J. K. Setlow, ed., Plenum Press, New York at pages 111–123. Specifically, the oligonucleotide probes in such microarrays are preferably synthesized by serially depositing individual nucleotides for each probe sequence in an array of "microdroplets" of a high tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes).

5.3.4. Target Polynucleotide Molecules

As described, supra, the polynucleotide molecules which may be analyzed by the present invention may be from any source, including naturally occurring nucleic acid molecules, as well as synthetic nucleic acid molecules. In a preferred embodiment, the polynucleotide molecules analyzed by the invention comprise RNA, including, but by no means limited to, total cellular RNA, poly(A)$^+$ messenger RNA (mRNA), fractions thereof, or RNA transcribed from cDNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–5299). In an alternative embodiment, which is preferred for S. cerevisiae, RNA is extracted from cells using phenol and chloroform, as described, in Ausubel et al. (Ausubel et al., eds., 1989, *Current Protocols in Molecular Biology*, Vol III, Green Publishing Associates, Inc., John Wiley & Sons, Inc., New York, at pp. 13.12.1–13.12.5). Poly(A)$^+$ RNA is selected by selection with oligo-dT cellulose. Cells of interest include, but are by no means limited to, wild-type cells, drug-exposed wild-type cells, modified cells, diseased cells and, in particular, cancer cells.

In one embodiment, RNA can be fragmented by methods known in the art, e.g., by incubation with $ZnCl_2$, to generate fragments of RNA. In one embodiment, isolated mRNA can be converted to antisense RNA synthesized by in vitro transcription of double-stranded cDNA in the presence of labeled dNTPs (Lockhart et al., 1996, *Nature Biotechnology* 14:1675).

In other embodiments, the polynucleotide molecules to be analyzed may be DNA molecules such as fragmented genomic DNA, first strand cDNA which is reverse transcribed from mRNA, or PCR products of amplified mRNA or cDNA.

5.3.5. Hybridization to Microarrays

As described supra, nucleic acid hybridization and wash conditions are chosen so that the polynucleotide molecules to be analyzed by the invention (referred to herein as the "target polynucleotide molecules") "specifically bind" or "specifically hybridize" to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York.

When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

6. EXAMPLE

The following example is presented by way of illustration of the previously described invention, and is not limiting of that description. The example illustrates how dissociation curves may be ranked according to their specificity for a particular probe according to the above described methods.

Wash series data were obtained for a perfect match and seven different mismatch duplexes of 20 base oligonucleotide probes. The nucleotide sequences of the eight oligonucleotide probes are provided in Table I below. In more detail, eight different 20 mer oligonucleotide probes (SEQ ID NOS:2–9), containing from zero to six mismatches with respect to a test oligonucleotide sequence (SEQ ID NO:1), were spotted onto a glass slide according to the following procedure: The oligonucleotides were synthesized with primary amino groups on their 3'-ends. A solution containing 5×SSC and 25 µM of the different oligonucleotides was spotted onto silylated (free aldehyde) microscope slides (CEL Associates, Houston, Tex.). After drying for 12 hours, the slides were washed twice in a 0.2% SDS solution and twice in water (one minute for each wash) to remove the excess salt and unbound DNA. The slides were then incubated in a 90 mM sodium borohydride solution to reduce the free aldehydes. The slides were then rinsed three times in a 0.2% SDS solution and twice in water (one minute for each wash).

TABLE I

| | | |
|---|---|---|
| Test Sequence | 5'-GAGACAGCTCTTCCGAACAT-3' | (SEQ ID NO:1) |
| Probe A (o) (perfect match) | 5'-ATGTTCGGAAGAGCTGTCTC-3' | (SEQ ID NO:2) |
| Probe B (x) (1 mismatch) | 5'-ATGTTCGG__G__AGAGCTGTCTC-3' | (SEQ ID NO:3) |
| | | (SEQ ID NO:4) |

TABLE I-continued

| | | |
|---|---|---|
| Probe C (*) (3 mismatches) | 5'-ATGTTCGGA__GAG__GCTGTCTC-3' | (SEQ ID NO:5) |
| Probe D (□) (4 mismatches) | 5'-ATGTT__G__GGAAGAG__G__TGT__G__TG-3' | (SEQ ID NO:6) |
| Probe E (4 mismatches) | 5'-__TT__GTTCGG__TT__GTGCTGTCTC-3' | (SEQ ID NO:7) |
| Probe F (4 mismatches) | 5'-__TT__GTTCGG__T__C__G__TGCTGTCTC-3' | (SEQ ID NO:8) |
| Probe G (♦) (5 mismatches) | 5'-__TT__GTTCGG__CCA__TGCTGTCTC-3' | (SEQ ID NO:9) |
| Probe H (▲) (6 mismatches) | 5'-A__AGAA__CGGAAGAGC__AG__AC__AC__-3' | |

Figure 4:
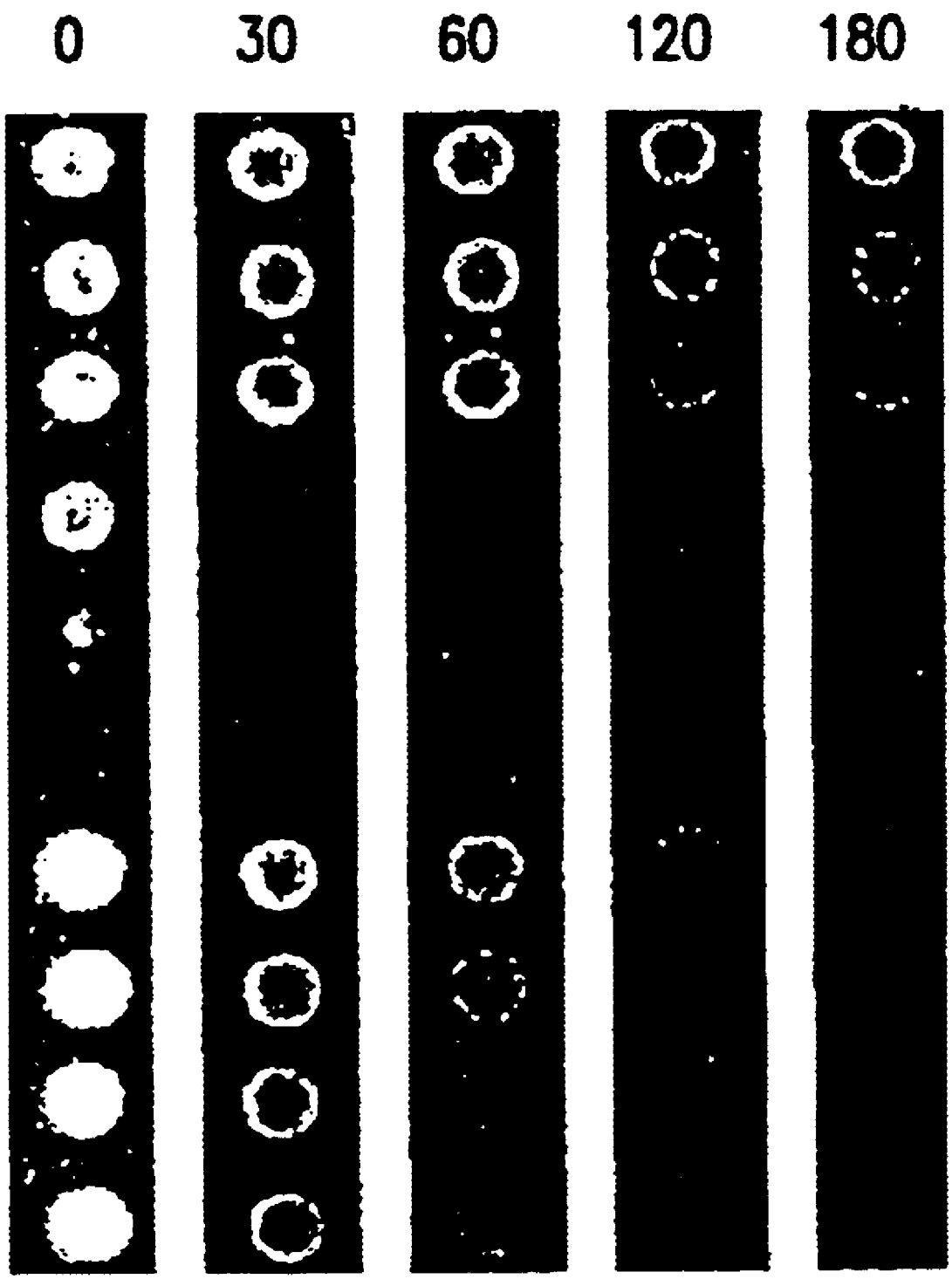
FIG. 4 shows fluorescent images of a glass slide spotted with DNA sequences A–H listed in Table II (SEQ ID NOS:2–9) after hybridization to a Cy3 labeled sequence complementary (SEQ ID NO:1) and washed for 30, 60, 120, and 180 seconds, respectively.

A Cy3 labeled test sequence (SEQ ID NO:1) was hybridized to one of the spotted slides for 20 minutes at 50° C. The 50 µl hybridization mixture contained 6×SSPE-T (0.9 M NaCl, 70 mM phosphate buffer pH 7.4, 7 mM EDTA, and 0.005% Triton-x 100) and 5 nM of the Cy3 labeled 20 mer. Following the hybridization, the glass slide was briefly rinsed with 4° C. 0.06×SSPE-T to remove the unbound oligonucleotides and salt. The slide was then scanned using a General Scanning ScanArray 3000 confocal scanner. To determine the off-rates for the different oligonucleotides, the slide was placed in a beaker containing 500 ml of 0.6× SSPE-T at 50° C. The slide was removed from the beaker, after wash times of 30, 60, 120, and 180 seconds, briefly rinsed with cold 0.06 SSPE-T, scanned, and returned to the beaker. The resulting images are shown in FIG. 4. The hybridization signals from these images were quantitated, and the data was used to determine the off-rates.

Figure 5:
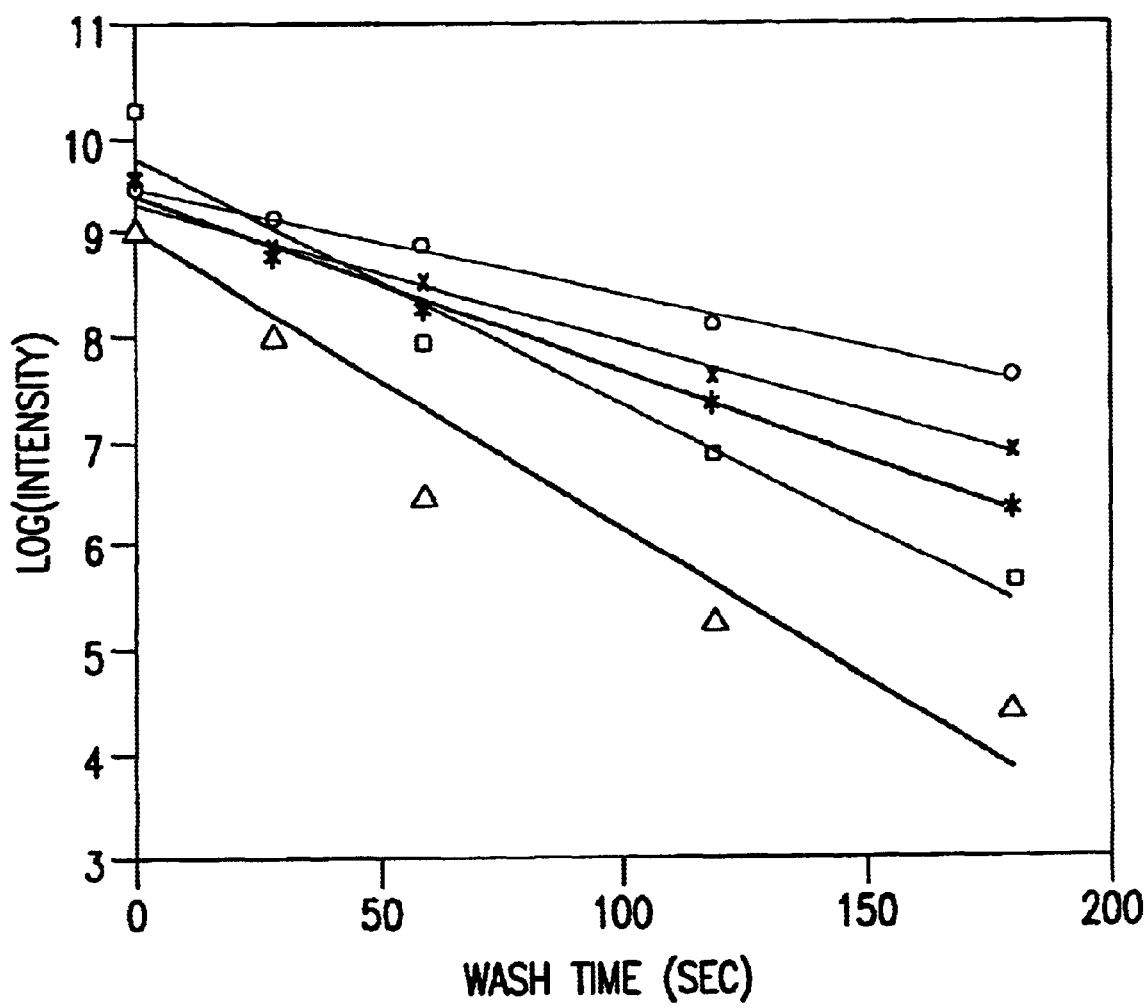
FIG. 5 is a plot of wash series data for perfect match (○) and five different mismatch duplexes: 1 mismatch (×), three mismatches (*), four mismatches (■), four mismatches (♦), and six mismatches (▼); the Log(Intensity) of each duplex is plotted vs. wash time, and is fit by an exponential decay model (straight lines).

FIG. 5 is a plot of the Log(Intensity) of the measured hybridization signal for five of the eight oligonucleotide probes (Probes A–D and G–H) vs. the wash time. The data was interpolated by fitting to an exponential decay model (i.e. Equation 5 in Section 5.1.3 above), and each curve was normalized to have the same value at the first wash point. The interpolated curve obtained from the perfect match was used as a reference dissociation curve to rate the specificity of each of the other probes for the test sequence. The objective reference metric Q was computed in linear intensity representation for each oligonucleotide probe whose hybridization signal is plotted in FIG. 5 (i.e., for probes A–D and G–H), according to Equation 9 in Section 5.1.3 above. The values obtained are listed in Table II below. As expected, the values of Q are a monotonic function of the specificity of each probe for the test sequence. The most specific probe (i.e., Probe A, the perfect match) has the lowest Q value (i.e., $Q^A=0$) since this curve is compared with itself. The other probes indicate steadily increasing values of the objective metric (i.e., of Q) with increasing degree of mismatch. The data thus indicates, as expected, that polynucleotide probes have progressively decreasing specificity for a sequence as the extent of base-pair mismatch to the probe increases.

TABLE II

| Polynucleotide Set | Mismatched Base-pairs | Q |
|---|---|---|
| A | 0 | 0.0 |
| B | 1 | 14.6 |
| C | 3 | 27.1 |

TABLE II-continued

| Polynucleotide Set | Mismatched Base-pairs | Q |
|---|---|---|
| D | 4 | 40.9 |
| G | 5 | 41.0 |
| H | 6 | 53.9 |

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A computer system for determining the specificity with which molecules of a given probe hybridize to a particular polynucleotide in a first polynucleotide sample that comprises a mixture of polynucleotide sequences, said computer system comprising
   a processor, and
   a memory coupled to said processor and encoding one or more programs,
   wherein the one or more programs cause the processor to perform a method comprising:
      comparing a dissociation curve representing dissociation, over time, of molecules of said first polynucleotide sample from molecules of the given probe to a reference dissociation curve representing dissociation, over time, of molecules of a second polynucleotide sample from a reference probers,
      wherein said comparing of the dissociation curve to the reference dissociation curve comprise determining the value of a metric representing the difference between the dissociation curve and the reference dissociation curve.

2. The computer system of claim 1 wherein the value of the metric is determined by subtracting the integral of the dissociation curve from the integral of the reference dissociation curve.

3. The computer system of claim 1 wherein the reference dissociation curve is read into the memory from a database.

4. The computer system of claim 1 wherein the programs cause the processor to calculate a theoretical prediction of the form of the dissociation curve.

5. The computer system of claim 4 wherein
the form of the dissociation curve comprises shape parameters, and
the programs cause the processor to adjust the shape parameters to match known dissociation curves.

6. The computer system of claim 5 wherein the known dissociation curves are read into the memory from a database.

7. A computer program product for use in conjunction with a computer having a processor and a memory connected to the processor,
said computer program product comprising a computer readable storage medium having a computer program mechanism encoded thereon,
wherein the computer program mechanism may be loaded into the memory of the computer and cause the processor to execute the steps of:
comparing a dissociation curve representing dissociation, over time, of molecules of said first polynucleotide sample from molecules of a given probe to a reference dissociation curve representing dissociation, over time, of molecules of a second polynucleotide sample from molecules of a reference probe,
wherein said comparing of the dissociation curve to the reference dissociation curve comprises determining the value of a metric representing the difference between the dissociation curve and the reference dissociation curve.

8. The computer program product of claim 7 wherein the computer program mechanism may further cause the processor to determine the value of the metric by subtracting the integral of the dissociation curve from the integral of the reference dissociation curve.

9. A method for determining the specificity with which molecules of a give n probe hybridize to a particular polynucleotide in a first polynucleotide sample that comprises a mixture of polynucleotide sequences, said method comprising:
comparing
a dissociation curve representing dissociation, over time, of molecules of said first polynucleotide sample from molecules of the given probe to
a reference dissociation curve representing dissociation, over time, of molecules of a second polynucleotide sample from molecules of a reference probe,
wherein said comprising of the dissociation curve to the reference dissociation curve comprises determining the value of a metric representing the difference between the dissociation curve and the reference dissociation curve.

10. The method of claim 9 wherein the metric is determined by subtracting the integral of the dissociation curve from the integral of the reference dissociation curve.

11. The method of claim 9 wherein the dissociation curve is provided by a method comprising:
(a) contacting the first polynucleotide sample to one or more molecules of the given probe under conditions which allow polynucleotide molecules in the first polynucleotide sample to hybridize to the given probe, and
(b) measuring polynucleotide molecules hybridized to the one or more molecules of the given probe over a time period wherein a detectable fraction of the polynucleotide molecules dissociates from the one or more molecules of the given probe.

12. The method of claim 11 wherein in the polynucleotide molecules in the first polynucleotide sample each have the same number of mismatches to the given probe.

13. The method of claim 11 wherein the first polynucleotide sample comprises a plurality of sets of polynucleotides, and wherein
each set of polynucleotides consists of polynucleotide molecules having the same number of mismatches to the given probe, and
the number of mismatches to the given probe is different for each set of polynucleotides.

14. The method of claim 13 wherein each set of polynucleotides contains polynucleotide molecules that are differentially labeled from polynucleotide molecules in the other sets.

15. The method of claim 13 wherein said step of measuring polynucleotide molecules hybridized to the given probe comprises measuring the polynucleotide molecules of a particular set of polynucleotides in said plurality of sets of polynucleotides hybridized to the given probe.

16. The method of claim 11 wherein the polynucleotide molecules are detectably labeled with a detectable label.

17. The method of claim 11 wherein the step of measuring the polynucleotide molecules hybridized to the one or more molecules of the given probe comprises:
(i) repeatedly washing the first polynucleotide sample under conditions such that some fraction of the polynucleotide molecules dissociates from the one or more molecules of the given probe; and
(ii) measuring the polynucleotide molecules that remain hybridized to the one or more molecules of the given probe after each washing.

18. The method of claim 9 wherein the reference dissociation curve is provided by a method comprising:
(a) contacting the second polynucleotide sample to one or more molecules of the reference probe under conditions which allow polynucleotide molecules in the second polynucleotide sample to hybridize to the reference probe; and
(b) measuring polynucleotide molecules hybridized to the one or more molecules of the reference probe over a time period wherein a detectable fraction of the polynucleotide molecules dissociates from the one or more molecules of the reference probe.

19. The method of claim 18 wherein the polynucleotide molecules are detectably labeled with a detectable label.

20. The method of claim 18 wherein the reference probe is identical to the given probe and wherein the first sample is different from the second sample.

21. The method of claim 18 wherein the reference probe has a binding energy for a perfect match duplex that is similar or identical to the binding energy of the given probe for a perfect match duplex.

22. The method of claim 18 wherein the polynucleotide molecules in the second polynucleotide sample each have the same number of mismatches to the reference probe.

23. The method of claim 18 wherein the second polynucleotide sample comprises a plurality of sets of polynucleotides, and wherein
each set of polynucleotides consists of polynucleotide molecules having the same number of mismatches to the reference probe, and
the number of mismatches to the reference probe is different for each set of polynucleotides.

24. The method of claim 23 wherein each set of polynucleotides contains polynucleotide molecules that are differentially labeled from polynucleotide molecules in the other sets.

25. The method of claim 23 wherein said step of measuring polynucleotide molecules hybridized to the one or more molecules of the reference probe comprises measuring the polynucleotide molecules of a particular set of polynucleotides in said plurality of sets of polynucleotides hybridized to the one or more molecules of the reference probe.

26. The method of claim 9 wherein:
   (a) the dissociation curve is provided by a method comprising:
      (i) contacting the first polynucleotide sample to one or more molecules of the given probe under conditions which allow polynucleotide molecules in the first polynucleotide sample to hybridize to the given probe; and
      (ii) measuring polynucleotide molecules hybridized to the one or more molecules of the given probe over a time period wherein a detectable fraction of the polynucleotide molecules dissociates from the one or more molecules of the given probe; and
   (b) the reference dissociation curve is provided by a method comprising:
      (i) contacting the second polynucleotide sample to one or more molecules of the reference probe under conditions which allow polynucleotide molecules in the second polynucleotide sample to hybridize to the reference probe; and
      (ii) measuring polynucleotide molecules hybridized to the one or more molecules of the reference probe over a time period wherein a detectable fraction of the polynucleotide molecules dissociates from the one or more molecules of the reference probe.

27. The method of claim 26 wherein
   the polynucleotide molecules in the first sample are detectably labeled with a first label, and
   the polynucleotide molecules in the second sample are detectably labeled with a second label,
   said second label being distinguishable from said first label.

28. The method of claim 26 wherein the reference probe is identical to the given probe and wherein the first polynucleotide sample is different from the second polynucleotide sample.

29. The method of claim 28 wherein the first polynucleotide sample comprises a plurality of sets of polynucleotides, and wherein
   each set of polynucleotides of the first polynucleotide sample consists of polynucleotide molecules having the same number of mismatches to the given probe, and
   the number of mismatches to the given probe is different for each set of polynucleotides of the first polynucleotide sample.

30. The method of claim 29 wherein each set of polynucleotides of the first polynucleotide sample contains polynucleotide molecules that are differentially labeled from polynucleotide molecules in the other sets of the first sample.

31. The method of claim 28 or 29 wherein said step of measuring polynucleotide molecules hybridized to the given probe comprises measuring the polynucleotide molecules of a particular set of polynucleotides of the first polynucleotide sample hybridized to the given probe.

32. The method of claim 29 wherein the polynucleotide molecules in the second polynucleotide sample each have the same number of mismatches to the reference probe.

33. The method of claim 32 wherein the polynucleotide molecules of a set of polynucleotides of the first sample have the same number of mismatches to the given probe as the number of mismatches that the polynucleotide molecules of the second polynucleotide sample have to the reference probe.

34. The method of claim 29 wherein the second polynucleotide sample comprises a plurality of sets of polynucleotides, and wherein
   each set of polynucleotides of the second polynucleotide sample consists of polynucleotide molecules having the same number of mismatches to the reference probe, and
   the number of mismatches to the reference probe is different for each set of polynucleotides of the second polynucleotide sample.

35. The method of claim 34 wherein the polynucleotide molecules of each set of polynucleotides of the first sample have the same number of mismatches to the given probe as the number of mismatches that the polynucleotide molecules of a set of polynucleotides of the second polynucleotide sample have to the reference probe.

36. The method of claim 34 wherein each set of polynucleotides of the second polynucleotide sample contains polynucleotide molecules that are differentially labeled from polynucleotide molecules in the other sets.

37. The method of claim 34, 35 or 36 wherein said step of measuring polynucleotide molecules hybridized to the reference probe comprises measuring the polynucleotide molecules of a particular set of polynucleotides of the second polynucleotide sample hybridized to the reference probe.

38. The method of claim 37 wherein the measured polynucleotide molecules of the particular set of polynucleotides of the second polynucleotide sample have the same number of mismatches to the reference probe as the number of mismatches that the polynucleotide molecules of a set of polynucleotides of the first polynucleotide sample have to the given probe.

39. The method of claim 28 wherein:
   (a) the first polynucleotide sample comprises polynucleotide molecules having a first number of mismatches to the given and reference probes; and
   (b) the second polynucleotide sample comprises polynucleotide molecules having a second number of mismatches to the given and reference probes,
   and wherein the first number of mismatches is different from the second number of mismatches.

40. The method of claim 26 wherein the reference probe is different from the given probe and wherein the first sample has the same composition as the second sample.

41. The method of claim 40 wherein:
   (a) the first polynucleotide sample comprises polynucleotide molecules having a first number of mismatches to the given probe; and
   (b) the second polynucleotide sample comprises polynucleotide molecules having a second number of mismatches to the reference probe,
   the first number of mismatches to the given probe being the same as the second number of mismatches to the reference probe.

42. The method of claim 26 wherein the polynucleotide molecules in the first polynucleotide sample are detectably labeled with a detectable label.

43. The method of claim 26 wherein the polynucleotide molecules in the second polynucleotide sample are detectably labeled with a detectable label.

44. The method of any one of claims 16, 19, 42 or 43 wherein the detectable label is a fluorescent label.

45. The method of claim 44 wherein the fluorescent label is fluorescein, rhodamine, texas red, or a derivative thereof.

46. The method of claim 44 wherein the fluorescent label is FAM, JOE, ROX, HX, TEr, IRD40, MD41, a cyarine dye, a BODIPY dye or an ALEXA dye.

47. The method of claim 46 wherein the fluorescent label isacyamne dye that is Cy2, Cy3, Cy3.5, Cy5, Cy5.5, Cy7 or FLUOMX.

48. The method of claim 46 wherein the fluorescent label is a BODIPY dye that is BODIPY-FL, BODIPY-TR, BODIPY-TMR, BODIPY-630/650 or BODIPY-650/670.

49. The method of claim 46 wherein the fluorescent label is a ALEXA dye that is ALFXA-488, AIEXA-532, ALEXA-546, ALEXA-569 or ALEXA-594.

50. The method of any one of claims 16, 19, 42 or 47 wherein the detectable label is a radioactive isotope.

51. The method of claim 50 wherein the radioactive isotope is $^{32}P$, $^{35}S$, $^{14}C$ or $^{125}I$.

52. The method of any one of claims 16, 19, 42 or 47 wherein the detectable label is an electron rich molecule.

53. The method of claim 52 wherein the electron rich molecule is ferritin, hemocyanin or colloidal gold.

54. The method of any one of claims 16, 19, 42 or 47 wherein the detectable label comprises a first chemical group specifically complexed to the polynucleotide molecule, and wherein the first chemical group is detected by a method comprising contacting the first chemical group with a second chemical group that:
(i) has binding affinity for the first chemical group; and
(ii) is covalently linked to an indicator molecule.

55. The method of claim 54 wherein the first chemical group is avidin or streptavidin, and wherein the second chemical group is biotin or iminobiotin.

56. The method of claim 9 wherein the reference dissociation curve is provided by a theoretical prediction of the form of the reference dissociation curve, and wherein shape parameters of the theoretical prediction are adjusted to match a dissociation curve of an equivalent polynucleotide set.

57. The method of claim 56 wherein one of said shape parameters is a dissociation time.

58. The method of claim 9 wherein polynucleotide molecules in the first or the second polynucleotide sample are naturally occurring polynucleotide molecules.

59. The method of claim 58 wherein the naturally occurring polynucleotide molecules comprise genomic DNA molecules, or fragments thereof, isolated from cells or from an organism.

60. The method of claim 58 wherein the naturally occurring polynucleotide molecules comprise RNA molecules, or fragments thereof, isolated from a cell or organism.

61. The method of claim 60 wherein the RNA molecules comprise messenger RNA molecules.

62. The method of claim 9 wherein polynucleotide molecules in the first or the second polynucleotide sample comprise synthetic nucleic acid molecules.

63. The method of claim 9 wherein polynucleotide molecules in the first or the second polynucleotide sample comprise cDNA molecules.

64. The method of claim 9 wherein polynucleotide molecules in the first or the second polynucleotide sample comprise polynucleotide molecules synthesized by polymerase chain reaction.

65. The method of claim 9 wherein polynucleotide molecules in the first or the second polynucleotide sample comprise short polynucleotide molecules that are representative of a nucleic acid population of a cell.

66. The method of claim 9 wherein the given probe comprises a nucleotide sequence that is complementary to a DNA sequence.

67. The method of claim 66 wherein the DNA sequence is a genomic DNA sequence.

68. The method of claim 66 wherein the DNA sequence is a cDNA sequence.

69. The method of claim 9 wherein the given probe comprises a nucleotide sequence that is complementary to an RNA sequence.

70. The method of claim 69 wherein the RNA sequence is a messenger RNA sequence.

71. The method of claim 9 wherein the given probe comprises a nucleotide sequence that is complementary to a STS.

72. The method of claim 9 wherein the given probe comprises a nucleotide sequence that is complementary to a SNP.

73. The method of claim 9 wherein the given probe comprises a nucleotide sequence or a DNA or RNA analog.

74. The method of claim 9 wherein the given probe is immobilized on a solid surface.

75. The method of claim 74 wherein the solid surface is a porous surface.

76. The method of claim 74 wherein the solid surface is a nonporous surface.

77. The method of claim 74 wherein the solid surface is a nylon membrane Or a cellulose filter.

78. The method of claim 74 wherein the solid surface is a glass surface.

79. The method of claim 74 wherein the given probe is part of an array of probes.

80. The method of claim 79 wherein the array of probes is a microarray.

81. The method of claim 80 wherein the microarray comprises binding sites for products encoded by fewer than 50% of the genes in the genome or an organism.

82. The method of claim 80 wherein the microarray comprises binding sites for products encoded by at least 50% of the genes in the genome of an organism.

83. The method of claim 82 wherein the microarray comprises binding sites for products encoded by at least 75% of the genes in the genome of the organism.

84. The method of claim 83 wherein the microarray comprises binding sites for products encoded by at least 85% of the genes in the genome of the organism.

85. The method of claim 84 wherein the microarray comprises binding sites for products encoded by at least 90% of the genes in the genome of the organism.

86. The method of claim 85 wherein the microarray comprises binding sites for products encoded by at least 99% of the genes in the genome of the organism.

87. The method of claim 80 wherein each probe of the microarray comprises a polynucleotide sequence of between 20 and 50,000 bases in length.

88. The method of claim 80 wherein each probe of the microarray comprises a polynucleotide sequence of between 300 and 1,000 bases in length.

89. The method of claim 80 wherein each probe of the microarray comprises a single stranded polynucleotide sequence of between 4 and 200 bases in length.

90. The method of claim 89 wherein the probes of the microarray are between 15 and 150 bases in length.

91. The method of claim 90 wherein the probes of the microarray are less than 40 bases in length.

92. The method of claim 91 wherein the probes of the microarray are between 15 and 30 bases in length.

93. The method of claim 90 wherein the probes of the microarray are between 40 and 80 bases in length.

94. The method of claim 93 wherein the probes of the microarray are between 40 and 70 bases in length.

95. The method of claim 94 wherein the probes are between 50 and 60 bases in length.

96. The method of claim 80 wherein the microarray comprises at least 500 different probes per 1 cm$^2$.

97. The method of claim 80 wherein the microarray comprises at least 1,000 different probes per 1 cm$^2$.

98. The method of claim 80 wherein the microarray comprises at least 1,500 different probes per 1 cm$^2$.

99. The method of claim 80 wherein the microarray comprises at least 2,000 different probes per 1 cm$^2$.

100. The method of claim 80 wherein the microarray comprises at least 2,500 different probes per 1 cm$^2$.

101. The method of claim 80 wherein the microarray comprises at least 10,000 different probes.

102. The method of claim 80 wherein the microarray comprises at least 15,000 different probes.

103. The method of claim 80 wherein the microarray comprises at least 20,000 different probes.

104. The method of claim 80 wherein the microarray comprises at least 25,000 different probes.

105. The method of claim 80 wherein the microarray comprises at least 50,000 different probes.

106. The method of claim 80 wherein the microarray comprises at least 55,000 different probes.

107. The method of claim 9 wherein the reference probe has a known specificity for the particular polynucleotide.

108. The method of claim 20 or 28 wherein the second polynucleotide sample consists essentially of molecules of a specific polynucleotide which hybridizes to the reference probe.

109. The method of claim 20 or 28 wherein the second polynucleotide sample consists essentially of molecules of a specific polynucleotide which hybridizes to, but which has one or more mismatches to, the reference probe.

110. The method of claim 20 or 28 wherein the second polynucleotide sample consists essentially of molecules of the particular polynucleotide in the first sample.

* * * * *

```
                        SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
gagacagctc ttccgaacat                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
atgttcggaa gagctgtctc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
atgttcggga gagctgtctc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
atgttcggag aggctgtctc                                              20

<210> SEQ ID NO 5
<211> LENGTH: 20
<212> TYPE: DNA
<213> ORGANISM: Artificial Sequence
<220> FEATURE:
```

-continued

```
<223> OTHER INFORMATION: Description of Artificial Sequence:
      Oligonucleotide

<400> SEQUENCE: 5
atgttgggaa gaggtgtgtg                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ttgttcggtt gtgctgtctc                                            20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
ttgttcggtc gtgctgtctc                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
ttgttcggcc atgctgtctc                                            20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
aagaacggaa gagcagacac                                            20
```